US011688497B2

(12) United States Patent
Shannon et al.

(10) Patent No.: US 11,688,497 B2
(45) Date of Patent: *Jun. 27, 2023

(54) SYSTEMS AND METHODS FOR PREDICTIVE DATA ANALYTICS

(71) Applicant: Express Scripts Strategic Development, Inc., St. Louis, MO (US)

(72) Inventors: Benjamin J. Shannon, St. Louis, MO (US); Bradley Kelley, St. Louis, MO (US); Karen P. Dean, Manalapan, NJ (US); Michael Looney, Edina, MN (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/897,696

(22) Filed: Aug. 29, 2022

(65) Prior Publication Data

US 2022/0415458 A1 Dec. 29, 2022

Related U.S. Application Data

(63) Continuation of application No. 16/988,915, filed on Aug. 10, 2020, now Pat. No. 11,430,548, which is a continuation of application No. 15/663,661, filed on Jul. 28, 2017, now Pat. No. 10,740,437.

(51) Int. Cl.
*G16H 10/60* (2018.01)
*G06Q 50/22* (2018.01)
*G06Q 40/08* (2012.01)

(52) U.S. Cl.
CPC ............. *G16H 10/60* (2018.01); *G06Q 40/08* (2013.01); *G06Q 50/22* (2013.01)

(58) Field of Classification Search
CPC ........ G06Q 40/08; G06Q 10/10; G16H 70/40; G16H 20/10
See application file for complete search history.

(56) References Cited

U.S. PATENT DOCUMENTS

| 8,185,413 | B2 | 5/2012 | Melnick |
| 8,666,926 | B1 | 3/2014 | Nease |
| 2006/0089862 | A1 | 4/2006 | Anandarao |
| 2015/0032465 | A1* | 1/2015 | Sundar .................. G16H 20/10 705/2 |

* cited by examiner

*Primary Examiner* — Joseph D Burgess
(74) *Attorney, Agent, or Firm* — Miller Johnson

(57) ABSTRACT

A system includes a processor and memory providing instructions for execution by the processor. The instructions include, responsive to a request from a user device indicating a group type and a time frame, selecting a set of users based on the group type. The instructions include retrieving the user data and historical data from a database and identifying a set of new users during the time frame. The instructions include adding the set of new users to the set of users and generating synthetic historical data for the set of users. The instructions include, based on the synthetic historical data for each user, computing a likelihood of discontinuation of a drugs and computing a likelihood of initiation of a drug. The instructions include estimating, for the group type, an aggregated output based on the likelihoods of initiation and discontinuation. The instructions include displaying the aggregated output on the user device.

18 Claims, 12 Drawing Sheets

SYSTEMS AND METHODS FOR PREDICTIVE DATA ANALYTICS

CROSS-REFERENCE TO RELATED APPLICATIONS

This application is a continuation of U.S. patent application Ser. No. 16/988,915 filed Aug. 10, 2020; said application is a continuation of U.S. patent application Ser. No. 15/663,661, filed on Jul. 28, 2017 and issued on Aug. 11, 2020 as U.S. Pat. No. 10,740,437; the entire disclosures of which are incorporated herein by reference.

BACKGROUND

Certain methods for predictive data analytics in certain industry areas such as health care apply actuarial techniques to aggregated historical data. Such techniques may be readily used in the industry, including, for example, when submitting annual information reports to particular organizations such as the Centers for Medicare & Medicaid Services ("CMS"). However, such aggregate methods may not result in accurate results due to certain limitations in the calculations.

BRIEF DESCRIPTION OF THE DRAWINGS

In the drawings, reference numbers may be reused to identify similar and/or identical elements.

DETAILED DESCRIPTION

Example systems and methods for predictive data analytics are described. In the following description, for purposes of explanation, numerous specific details are set forth in order to provide a thorough understanding of example embodiments. It will be evident, however, to one of ordinary skill in the art that these embodiments may be practiced without these specific details.

A pharmacy benefit manager (sometimes referred to herein as a "PBM") is a third party administrator of prescription drug plans for a variety of different types of customers including Medicare Part D, commercial health plans, and self-insured employer plans, among others. A pharmacy benefit manager can use financial models that provide for a narrow business margin in which inaccuracies in information related to drug or plan member profitability could have a significant impact on the business case for the overall prescription drug plan.

Current methods for forecasting the profitability of prescription drug plans apply actuarial techniques to aggregated historical data. Such techniques are standard in the industry and are used when submitting annual bids to organizations such as the Centers for Medicare & Medicaid Services ("CMS"). However, such aggregate methods fail to consider factors which may be used in forecasting the overall spend of a prescription drug plan, e.g., which individual plan members take a particular drug.

The present systems and methods described herein provide for accurate predictions of events in a prescription drug plan over time, e.g., future likelihoods of changes within the prescription drug plan. The changes in the drug plan may include additions of members to the plan, the likelihood of members using the plan, and the likelihood of how members will use the plan. The systems and methods may model the change to the prescription drug plan and gauge effects to the plan with increased accuracy by using virtual or simulated data that represents possible changes or the likelihood of possible changes within the plan over a period of time. Some prior predictive models would merely use past performance of the plan but do not take into account possible changes, e.g., enrollment of new plan members and the dis-enrollment of plan members. Embodiments of the systems and methods described herein may use the virtual or simulated data related to predicted enrolled members and/or dis-enrolled members as predicted by various models.

Figure 1:
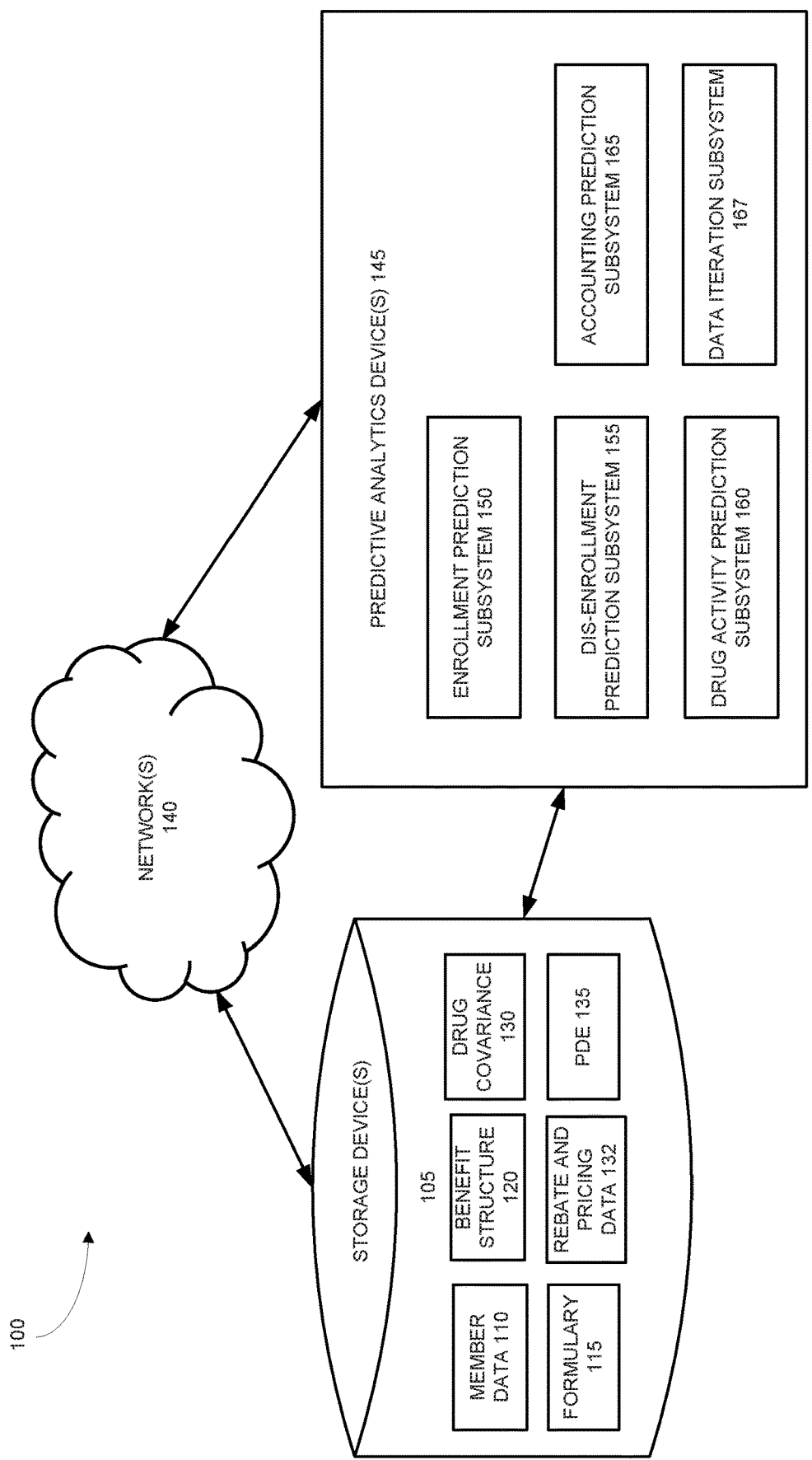
FIG. 1 is a diagram of an example implementation of a system for predicting drug events within a drug plan, according to an example embodiment.

FIG. 1 is a block diagram of a predictive analytics system 100, according to an example embodiment. The system 100 includes a predictive analytics device 145 in communication with a storage device 105 over a network 140. The predictive analytics device 145 is used by a device operator. The predictive analytics device 145 may be a stand-alone device that solely provides at least some of the functionality to enable risk adjustment pharmacy modeling.

Examples of the predictive analytics device 145 include a set-top box (STB), a receiver card, a mobile telephone, a personal digital assistant (PDA), a display device, a portable gaming unit, and a computing system, etc. Other devices, however, may also be used. In some embodiments, the predictive analytics device 145 may include a mobile computing device. For example, the predictive analytics device 145 may include a mobile electronic device, such an iPhone or iPad by Apple, Inc., mobile electronic devices powered by Android by Google, Inc., and a Blackberry by BlackBerry Limited. The predictive analytics device 145 may also include other computing devices, such as desktop computing devices, notebook computing devices, netbook computing devices, gaming devices, and the like. Other types of electronic devices may also be used.

The predictive analytics device 145 is a device operated by an entity that is at least partially responsible for creation and/or management of a pharmacy or drug benefit plan. While such entity operating the predictive analytics device 145 is typically a pharmacy benefit manager (PBM), other entities may operate the prescription drug plan prediction device 145 on behalf of themselves (i.e., the PBMs) or other entities. For example, the predictive analytics device 145 may be operated by a health plan or entity providing the health plan, a retail pharmacy chain, a drug wholesaler, a data analytics entity, or other type of software-related company, etc., or the like. In some embodiments, a PBM that provides the pharmacy benefit may also provide one or more than one additional benefits including a medical or health benefit, a dental benefit, a vision benefit, a wellness benefit, a radiology benefit, a pet care benefit, an insurance benefit, a long term care benefit, a nursing home benefit, etc., and the like. The PBM may, in addition to its PBM operations, operate one or more than one pharmacies. The pharmacies may be retail pharmacies, mail order pharmacies, etc.

Some of the operations of the PBM that operates the predictive analytics device 145 may include the following activities and processes. A member (or a person on behalf of the member) of a pharmacy benefit plan may obtain a prescription drug at a retail pharmacy location (e.g., a location of a physical store, etc.) from a pharmacist or a pharmacist technician. The member may also obtain the prescription drug through mail order drug delivery from a mail order pharmacy location, which may be the pharmacy system 100. In some embodiments, the member may obtain the prescription drug directly or indirectly through the use of a machine, such as a kiosk, vending unit, mobile electronic device, or a different type of mechanical, electrical, electronic communication device and/or computing device. Such a machine may be filled with the prescription drug in prescription packaging, which may include multiple prescription components, by the system 100. In some embodiments, the pharmacy benefit plan is administered by or through the predictive analytics device 145.

The member may have a copayment for the prescription drug that reflects an amount of money that the member is responsible to pay the pharmacy for the prescription drug. The money paid by the member to the pharmacy may come from personal funds of the member, a health savings account (HSA) of the member or the member's family, a health reimbursement arrangement (HRA) of the member or the member's family, a flexible spending account (FSA) of the member or the member's family, etc., or the like. In some instances, an employer of the member may directly or indirectly fund or reimburse the member for the copayments.

The amount of the copayment required by the member may vary with different pharmacy benefit plans having different plan sponsors or clients and/or for different prescription drugs. The member's copayment may be a flat copayment (e.g., $10, etc.), co-insurance (e.g., 10%, etc.), and/or a deductible (e.g., for first $500 of annual prescription drug expense, etc.) for certain prescription drugs, certain types and/or classes of prescription drugs, and/or all prescription drugs. The copayment may be stored in the storage device 105 or determined by the predictive analytics device 145.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels used for the prescription drug to be received. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM, e.g., the predictive analytic device 145, may perform certain adjudication operations including verifying eligibility for the member, identifying/reviewing an applicable formulary for the member to determine any appropriate copayment, coinsurance, and deductible for the prescription drug, and performing a drug utilization review (DUR) on the member. Further, the PBM may provide a response to the pharmacy, e.g., the system 100, following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated.

The aforementioned adjudication operations generally occur before the copayment is received and the prescription drug is dispensed. However, in some instances, these operations may occur simultaneously, substantially simultaneously, or in a different order. In addition, more or less adjudication operations may be performed as at least part of the adjudication process.

The amount of reimbursement paid to the pharmacy by a plan sponsor and/or money paid by the member may be determined at least partially based on types of pharmacy network in which the pharmacy is included. In some embodiments, the amount may also be determined based on other factors. For example, if the member pays the pharmacy for the prescription drug without using the prescription or drug benefit provided by the PBM, the amount of money paid by the member may be higher than when the member uses the prescription or drug benefit. In some embodiments, the amount of money received by the pharmacy for dispensing the prescription drug and for the prescription drug itself may be higher than when the member uses the prescription or drug benefit. Some or all of the foregoing operations may be performed by executing instructions stored in the predictive analytics device 145 and/or an additional device.

Examples of the networks 104 include Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. The networks 104 may include optical network. The networks 104 may be a local area network or a global communication network, such as the Internet. In some embodiments, the networks 104 may include a network dedicated to prescription orders, e.g., a prescribing network such as the electronic prescribing network operated by Surescripts of Arlington, Va. The multiple networks 140 may communicate in series with each other to link the predictive analytics device 145 and the storage device 105 or in parallel to link the predictive analytics device 145 and the storage device 105. In some embodiments, the network 104 is a single network.

The storage device 105 may include: a non-transitory storage (e.g., memory, hard disk, CD-ROM, etc.) in communication with the predictive analytics device 145, the directly and/or over the network 104. The storage device may be configured to store certain benefit data representative of multiple patients. The benefit data may be for patients who are members of a benefit plan. In an example embodiment, the benefit data may also be modified to include benefit data for non-plan members. The benefit data for non-members may be used to determine benefit data for synthetic members that may be enrolled in the benefit plan in the future or dis-enrolled in the future. In an example embodiment, the data for non-members can be used to train a model, which can be used by the plan to predict likelihood of future plan performance. The benefit data may also be for actual plan members or representative plan members. Representative plan members are generated statistical representations of possible, predicted or probable plan members. The benefit data stored by non-transitory storage of the storage device 105 may include member data 110, formulary data 115, benefit structure data 120, drug covariance data 130, rebate and pricing data 132, and prescription drug event (PDE) data 135. Further, the system 100 may include additional devices, which may communicate with each other directly or over the network 104.

The member data 110 may include data related to each individual member of the plan or of multiple plans. The member data 110 may identify the member and the plan of which the member is part. The information stored as member data 110 may include personal information, personal health information, protected health information, and the like. Examples of the member data 110 may include name, address, telephone number, e-mail address, prescription drug history, etc., and the like. The member data 110 may include a plan sponsor identifier that identifies the plan sponsor associated with the member and/or a member identifier that identifies the member to the plan sponsor. The member data 110 may include a member identifier that identifies the plan sponsor associated with the patient and/or a patient identifier that identifies the patient to the plan sponsor. The member data 110 may also include, by way of example, dispensation preferences such as type of label, type of cap, message preferences, language preferences, or the like. The member data 110 may include medical claims, dental claims, wellness claims, or other type of health care-related claims for members. Other data may also be included in the member data 110.

For example, the member data 110 can include demographic data that represents information about members of a benefit plan, such as a pharmacy benefit plan that is managed by a pharmacy benefit manager. The demographic data can include ages of members of the plan, relative age indications of the members (e.g., the percentiles of the ages of different members relative to the entire plan population or relative to a group of members in the plan that does not include all members in the plan), risk scores provided by Centers for Medicare & Medicaid Services (or provided by other entities), relative risk indications of the members (e.g., the percentiles of the risk scores of different members relative to the entire plan population or relative to a group of members in the plan that does not include all members in the plan), genders of members in the plan, locations of members (e.g., states, towns, cities, counties, zip codes, street addresses, etc.), prescription drug plan products that the members are subscribed to, indications of whether the members qualify for low income status as defined by guidelines of the Centers for Medicare & Medicaid Services, and/or other information associated with different members that can be used to individually characterize the different members.

The formulary data 115 can include data representing a drug formulary, such as a listing of drugs that may be prescribed with a plan. Each plan may have its own formulary that may have drugs in common with other plans and may have drugs that are not part of another plan.

The benefit structure data 120 may include an algorithm of the instructions to be executed in a machine to implement a benefit plan. The instructions can relate to the plan and the prescription drug coverage for a group within a plan, and how the coverage applies to a member of the plan, either actual member or a simulated member used to predict likelihood of plan performance.

The drug covariance data 130 includes relationships of drugs that may be part of the plan or be prescribed to a member. The drug covariance data 130 includes covariance between different drug types. For example, the drug covariance data 130 can indicate whether a member is taking one type of drug, how likely the member is to also be taking a different type of drug based on another prescribed drug, and/or how likely the member is to also be taking a different type of drug based on a medical condition or diagnosis of the member. For example, some groups of different medications may be commonly prescribed together. This data is used in the stochastic simulations as described herein. The correlating of the drugs is based on historical likelihood that if a first drug is prescribed, then at least one second drug is also prescribed. Correlation can be the mutual or reciprocal relation of two or more drugs that are used together to treat a member or virtual member.

The covariance relationships may include imposed drug correlations rules for correlating drugs to other drugs. The drug covariance data 130 may also include the joint variability relationships between portions of the data stored in the storage devices 105. The covariance data 130 may include algorithms and/or instructions that include determining a historical patient-wise covariance between utilization of different pharmaceutical groups based on the drug history data; or to utilize linear algebra techniques to impose the historical patient-wise covariance during application of a stochastic model. The covariance data 130 may also store results from these algorithms. The drug covariance data 130 may be calculated from the prescription drug event data 135 and the member data 110.

Rebate and pricing data 132 reflects various rebates and pricing data for each plan, for each group of patients or other groupings.

The prescription drug event data 135 may include data relating to any individual member filing a prescription. The prescription drug event data 135 may include the type of the prescription drug (e.g., drug name and strength) and quantity of the prescription drug for each member. The prescription drug event data 135 may include the location of the pharmacy used by the member to fill the order. This prescription drug event data 135 may also include the dates at which the prescription was filled. The data can be used to model the season demand for a particular drug for a plan. The prescription drug event data 135 can also include the prescription drug cost and payment data. The prescription drug event data 135 can include a drug benefit type.

In some embodiments, prescription drug events include changes to members in a benefit plan. For example, a member enrolling into (e.g., entering) a pharmacy benefit plan can be one type of prescription drug event. A member dis-enrolling from (e.g., leaving) the pharmacy benefit plan can be another type of prescription drug event. A member being prescribed a first medication can be another type of prescription drug event. A member being prescribed a different, second medication based on or responsive to being prescribed the first medication can be another type of prescription drug event. A member ceasing to take a prescribed medication can be yet another type of prescription drug event.

In some embodiments, the predictive analytics device 145 may be housed on a server, e.g., with dedicated, specific processors and memory. The predictive analytics device 145 is configured to forecast multiple potential outcomes of a prescription drug plan at any point in time under a variety of different scenarios. These outcomes may be generated by selecting various prediction subsystems such as an enrollment prediction subsystem 150, a dis-enrollment prediction subsystem 155, a drug activity prediction subsystem 160, an accounting prediction subsystem 165, and a data iteration subsystem 167, some or all of which may be housed within the predictive analytics device 145. Each of these prediction subsystems will now be described in more detail.

Figure 2:
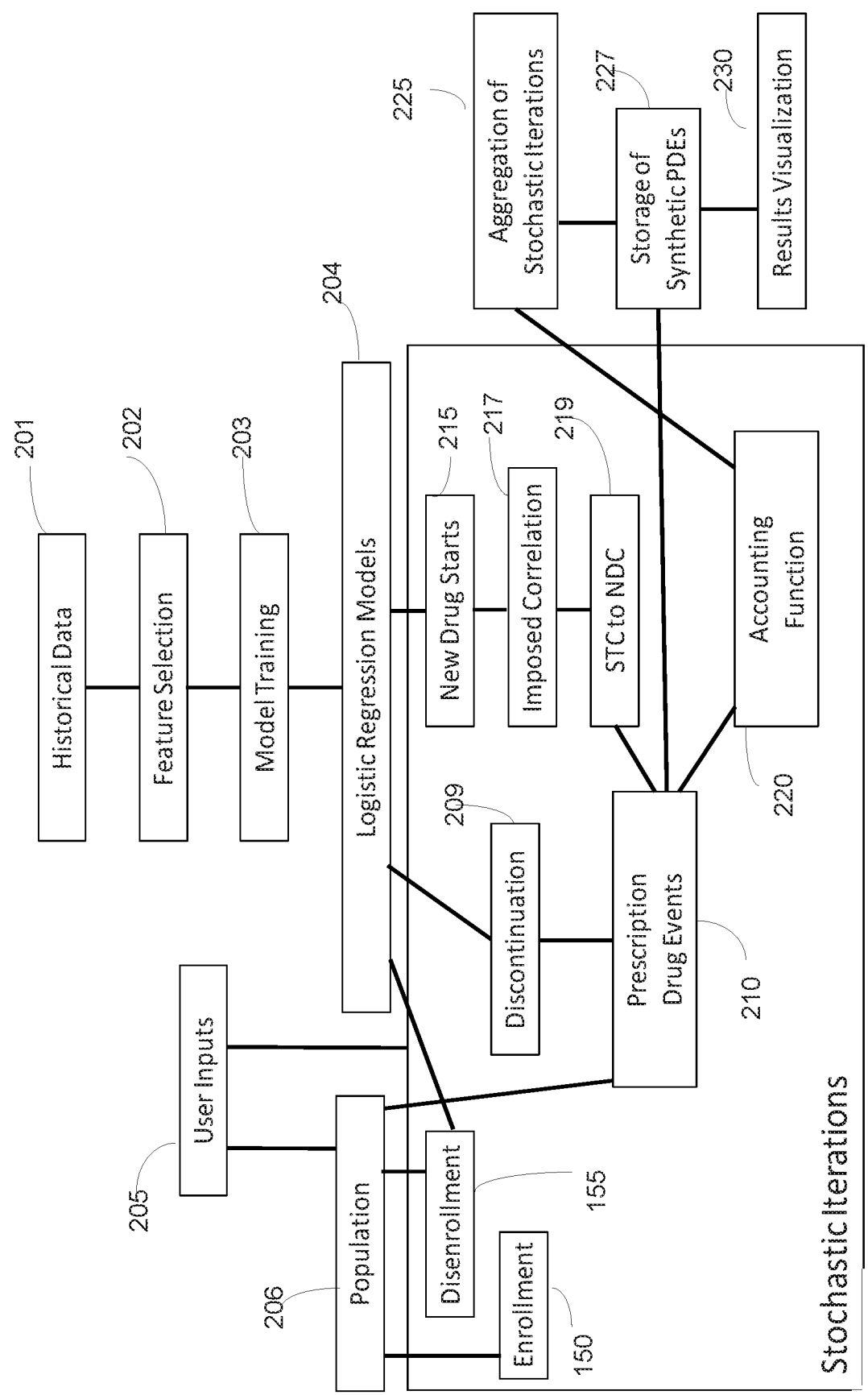
FIG. 2 is a flow diagram of an example implementation for predicting drug events, according to an example embodiment.

FIG. 2 shows a flow diagram 200 for predicting prescription drug events. The flow diagram 200 can represent operations and/or utilization of the prediction device 145 shown in FIG. 1. Certain medical events may require certain prescription drugs. The predicting of events may be based on a model or algorithm that is derived or proven from historical data 201. The historical data 201 can be empirically determined previous prescription drug events, such as how many members enrolled into a benefit plan, how many members dis-enrolled from the benefit plan, how many members in the plan were prescribed a first medication, how many members in the plan were prescribed a different, second medication based on being prescribed the first medication, how many members discontinued consuming or otherwise taking a prescribed medication, etc., during a previous period of time (e.g., during the previous month, quarter year, year, etc.). The flow diagram 200 reflects receipt of the historical data 201, which represents information relating to a medical plan or a prescription drug plan. The historical data 201 can include the prescription drug event data 135 and/or the member data 110 shown in FIG. 1. In some embodiments, the historical data 201 can include for several individual levels (e.g., for each of individual members of a plan) an aggregate historical time period total drug spend, an aggregate historical time period net insurance margins, and/or an individual level aggregate historical time period total number of prescription drug events. The aggregate historical time period total drug spend for a member represents the total amount of monies spent by a member within the defined or selected time period of medications under or within the plan (e.g., copays and/or deductibles). The aggregate historical time period net insurance margin for a member represents the difference between the premiums charged for the plan and the costs or expenses for providing the plan to that member during the defined or selected time period. The aggregate historical time period total number of prescription drug events for a member represents the number of prescription drug events of that member during the defined or selected time period.

The prediction device 145 can obtain the historical data 201 associated with a selection of a patient population in the plan. This selection can be the entire population of members in the plan, a targeted population of the plan (e.g., a user-selected subset of the members in the plan), or a random or pseudorandom subset of members in the plan. In another example embodiment, the historical data 201, when used to train the model, can include medical/pharmaceutical data for persons who are patients of a pharmacy but are not members in the pharmacy benefit plan being provided by the PBM, or that is subject to the calculation to determine the prescription/medical event(s). For example, these patients may obtain drug directly from the pharmacy, through a private label service offered by the pharmacy, the high-volume fulfillment center, or otherwise with the prescription drug data being stored in the present system and can be used to train a model. Thus, the models for predicting drug events may be determined using actual data, e.g., the historical data, or actual data combined with some virtual data. The virtual data would represent data, e.g., prescription drug event data and member data from virtual members of the prescription drug plan. In an example, embodiment, the system would create avatars representing statistically possible people and their prescription drug data for the historical data 201 to train a model.

At a feature selection block 202, the device 145 may select the types of data from the historical data 201 that will be used to train the model(s). In some data sets, the historical data 201 can be over one hundred different data types, and in some cases five hundred or more data types. At the feature selection block 202, a selection of one or more than one data type that are most relevant to each outcome prediction may be made. Results from operations at the feature selection block 202 may include a subset of relevant inputs, the data types, to train and to construct the model. Operations performed at the feature selection 202 block can be based on various methods to perform feature selection, e.g., least absolute shrinkage and selection, ridge regression, simulated annealing, best-first, genetic algorithms, greedy forward selection, or the like.

Operations performed at the predictive model trainer block 203 use the selected data from the feature selection block 202 that selects the historical data 201 to fit a logistic regression curve. This curve describes the relationship between multiple input variables (member demographics and drug history) and output variables of interest, viz. dis-enrollment subsystem 155, drug discontinuation block 209, and new drug start block 215.

The model can be trained using a variety of historical data of the plan and/or members in the plan. For example, the model can be created based on historical demographic data of the plan, historical drug history data of the plan, individual level aggregate historical time period total drug spends, individual level aggregate historical time period net insurance margins, and/or individual level aggregate historical time period total numbers of prescription drug events. The logistic regression function can be trained on multiple training set patients, where the training set patient of the training set patients is associated with an individual level aggregate historical time period total drug spend of the aggregate historical time period total drug spend, an individual level aggregate historical time period net insurance margins of the individual level aggregate historical time period net insurance margins, and an individual level aggregate historical time period total number of prescription drug events of the individual level aggregate historical time period total number of prescription drug events. This can help to ensure that the model is based on the previous data and prescription drug events of actual members in the plan.

In some embodiments, the model can be trained using a benefit plan structure of the plan, such as the benefits that are paid under the plan for various medications or services. The model also can be trained using individual level benefit plan phases and/or a formulary associated with the plan.

Operations performed at the logistic regression models block 204 creates and stores by the device 145 logistic regression models. The logistic regression models represent a machine learning technique that is executed by the machine to compute the model. Other machine learning can be used in place of logistic regression, e.g., neural networks, decision trees, support vector boosts, gradient boosts, or the like.

In one embodiment, one or more of the models 205 are created by the device 145 selecting demographic data and baseline data of a population subset of a discrete data environment (e.g., accessing demographic and baseline data for a subset of all members of a benefit plan. The population subset can represent those members that match an enrollment criterion of the plan during a defined or designated time period (e.g., those members being employed by the same employer, having at least a minimum age, etc.). The baseline data can be likelihoods or probabilities that various prescription drug events will or will not occur. For example, the baseline data can include a probability that any given individual member has a designated percentage chance of enrolling in the plan during the designated time period, that any given individual member has a designated percentage chance of exiting the plan during the designated time period, that any given individual member has a designated percentage chance of being prescribed with one or more first medications during the designated time period, and/or that any given member has a designated percentage chance of being prescribed an additional second medication based on the prescription of the first medication(s). The baseline data can be based on or represent empirical measurements of the same percentages of such prescription drug events. For example, the baseline data can be derived by calculating the percentage of members having a designated set of demographic data (e.g., age, gender, location, etc.) that enrolled into the plan during the preceding time period (e.g., during the preceding year), the percentage of members having the designated set of demographic data that exited out of the plan during the preceding time period, the percentage of members having the designated set of demographic data that were prescribed the first medication, and/or the percentage of members having the designated set of demographic data that also were prescribed the second medication. The model is based on or represents the set of demographic data and baseline data accessed by the device 145. One or several models can be created with different demographic data, different baseline data, and/or different population subsets.

Stochastic iterations can be performed by a data iteration subsystem 167 of the prediction device 145 using the models, user input from the user input 205 and a member population 206. Stochastic iterations are multiple runs of an algorithm in which various prescription drug events are simulated with a given probability. In an example embodiment, the stochastic model is fed the fact that an individual member has a 2% chance of taking a given prescription; the model will have that member taking that drug in about 2 out of 100 simulations. An enrollment prediction subsystem 150 feeds the predicted new enrollees (e.g., virtual members) into the member population 206. Based on the demographic data and the baseline data, the data iteration subsystem 167 determines how many members are likely to meet the enrollment criteria of the plan and thereby enroll into the plan (or will enroll into the plan) during the upcoming designated period of time. For example, the baseline data can indicate that persons reaching sixty-five years old within the upcoming period of time have a very high percentage of enrolling into a benefit plan, while persons reaching a younger age (e.g., sixty-two years old) have a lower percentage of enrolling. During each stochastic iteration of the model, the enrollment prediction subsystem 150 can randomly determine if each member enrolls into the plan based on this percentage and the demographic data. Because the iterations are randomly determined based on the percentage likelihood of enrollment during each iteration, the number of new members that are predicted to enroll in the plan during each iteration may be different.

The dis-enrollment prediction subsystem 155 takes as input the logistic regression model 204, and calculates the probability that each plan member will leave the plan in a selected time period. During each stochastic iteration, these probabilities are resolved to events which either happen or do not happen with the appropriate frequency. The selected time period may be over the course of a month, a plan year, or longer. This modified member population 206 can be used to determine predicted prescription drug events 210.

Based on the demographic data and the baseline data, the dis-enrollment prediction subsystem 155 determines how many members are likely to leave or otherwise dis-enroll from the plan during the upcoming designated period of time due to the members no longer meeting the enrollment criteria for a pharmacy benefit plan. For example, the baseline data can indicate that persons living in certain locations and/or being younger have a higher percentage of leaving the pharmacy benefit plan relative to persons living in other locations and/or being older.

During each stochastic iteration of the model, the dis-enrollment prediction subsystem 155 can randomly determine if each member leaves the plan based on this percentage and the demographic data. Because the iterations are randomly determined based on the percentage likelihood of dis-enrollment during each iteration, the number of members that are predicted to dis-enroll from the plan during each iteration may be different.

A discontinuation prediction subsystem 209 operates in a similar way to the dis-enrollment prediction subsystem 155. The discontinuation prediction subsystem 209 can be part of or can represent the drug activity prediction subsystem 160. Based on the logistic regression models, the discontinuation prediction 209 calculates the probability that each member who is currently taking a type of prescription drug will stop taking that drug during the selected time period. During each stochastic iteration, these probabilities are resolved to events which either happen or do not happen with the appropriate frequency. Based on the demographic data and the baseline data, the discontinuation 209 determines how many members are likely to stop taking a prescribed medication.

For example, the baseline data can indicate that persons of a designated age and/or having a designated income level (e.g., from the demographic data) have a lower likelihood of discontinuing consumption of a prescribed medication relative to persons not of the designated age and/or outside of the designated income level. During each stochastic iteration of the model, the discontinuation prediction 209 can randomly determine if each member stops consuming a prescribed medication based on this percentage and the demographic data. Because the iterations are randomly determined based on the percentage likelihood of medication cessation during each iteration, the number of members that are predicted to stop taking a prescribed medication during each iteration may be different.

A new drug starts 215 of the drug activity prediction subsystem 160 operates in a similar way to the dis-enrollment and discontinuation. Based on the logistic regression models, the new drug starts 215 calculates the probability that each member who is not currently take a type of prescription drug will start taking that drug during the selected time period. During each stochastic iteration, these probabilities are resolved to events which either happen or do not happen with the appropriate frequency. The new drug starts 215 differs from 155 and 209 in that it imposes statistical relationships between new drug starts. In the real world, a patient who has a medical event often begins taking two or more prescription drugs as a result of that event, and it is imperative that the model capture this relationship rather than treat new drug starts independently of one another. An imposed correlation 217 of the drug activity prediction 160 implements these statistical relationships. The imposed correlation 217 is trained by the historical covariance between each pair of drug classes. During each iteration of the stochastic model, linear algebra techniques (Leisch et al., 1998) are used to re-impose this pairwise covariance in the simulated prescription drug events.

For example, the baseline data can indicate that persons of a designated age and/or gender have a higher likelihood of being prescribed a first medication relative to persons of another age and/or another gender. During each stochastic iteration of the model, the new drug starts 215 can randomly determine if each member will be prescribed the first medication based on this percentage and the demographic data. Because the iterations are randomly determined based on the percentage likelihood of prescribing the first medication during each iteration, the number of members that are predicted to be prescribed the first medication during each iteration may be different.

Additionally, the imposed correlation 217 determines how likely a second and/or additional medications are to be prescribed to a member having designated demographic data responsive to that same member being prescribed the first medication. This likelihood can be empirically determined from the historical data 201. For example, a Type I diabetic may be prescribed insulin to control blood glucose levels of the diabetic, and also is likely to be prescribed a statin to keep the cholesterol levels of the diabetic within limits. During each stochastic iteration of the model, the new drug starts 215 can randomly determine if each member will be prescribed the second medications (or additional medications) based on or responsive to the member being prescribed one or more than one other medications. Because the iterations are randomly determined based on the percentage likelihood of prescribing the second or additional medications during each iteration, the number of members that are predicted to be prescribed the second or additional medications during each iteration may be different.

Individual prescription drug events, both real and simulated, are organized at the level of National Drug Code ("NDC"). There are roughly 100,000 distinct NDCs. The logistic regression models underlying the discontinuation prediction 209 and new drug start subsystem 215 are trained at the level of Specific Therapeutic Class (STC) code, a more general classifier with about five hundred distinct types. When the stochastic model has determined that a patient will begin taking a drug in a particular STC, an STC to NDC device 219 of the prediction 145 makes a prediction about which specific drug that patient will begin taking. The STC to NDC 219 is trained using historical data 201. For each new STC event, the STC to NDC 219 predicts the number of distinct NDCs, the codes, and the prices associated with the STC event. This information is combined to create a synthetic PDE.

New synthetic PDEs, as well as ongoing PDEs which were determined not to discontinue by the discontinuation device, are stored (e.g., as prescription drug events 210, which can be the same as the prescription drug event data 135 shown in FIG. 1).

The subsystems, devices, and an accounting processor can operate stochastically over multiple iterations to determine multiple probabilities. Each of these can perform multiple iterations to either determine a model or determine the results of a model.

Synthetic data is generated by the stochastic iterations described above. This synthetic data can be synthetic historical data of members as the synthetic data represents likelihoods that various prescription drug events will occur. The synthetic historical data can include synthetic event data (e.g., how likely various prescription drug events are to occur), synthetic demographic data (e.g., the likely demographic data of members predicted to be in the plan), and/or synthetic chemical composition history data (e.g., predictions of which medications are likely to be prescribed to the members in the plan).

Following completion of each stochastic iteration, the accumulated prescription drug events are sent to the accounting processor 220 of the accounting prediction subsystem 165 of the prediction device 145, which can represent a single processor or multiple processors. The accounting processor 220 processes each member's prescription drug events and adjudicates the prescription drug events through an insurance benefit structure, e.g. the Medicare Part D benefit structure. The cost of each prescription drug event is allocated to different buckets (Copay, Manufacturer, Plan Sponsor, Medicare) according to the benefit structure rules. Costs for each member and each bucket are aggregated across the entire plan population to give calculates of quantities such as total drug spend, net plan margin, etc.

For example, many stochastic iterations can be run by the prediction device 145 to determine how many members are likely to experience prescription drug events, such as how many members are likely to enroll into a plan, how many members are likely to leave the plan, how many members are likely to discontinue consumption of a prescribed medication, how many members are likely to be prescribed a first medication, and/or how many members are likely to be prescribed a second or additional medications based on receiving a prescription for another medication (e.g., the first medication). The predicted prescription drug events for the members can be associated with the demographic data of the members. The defined benefits of a benefit plan (e.g., copay costs, deductibles, amounts covered by the insurance company offering the plan, etc.) can be compared with the prescription drug events by the accounting processor 220 to determine how much each member is likely to pay for the copays and deductibles, and how much the entity offering the plan is likely to pay for the amounts over the deductibles and other costs. The total costs to the members in the plan and/or to the provider of the plan can be calculated by the accounting processor 220 of the prediction device 145 as an aggregate measure of the plan.

Synthetic PDEs may also be stored individually to facilitate later detailed inspection and visualization (Devices 227 and 230).

A visualization device 230 can process the synthetic prescription drug events with the aggregations to transmit or display the results at displays that are remote from the processing. The displayed visualizations may be interactive with multiple layers of data. In an example embodiment, the visualization output on a display device may include a distribution histogram showing the likelihood of different plan level outcomes. For example, the visualization may show that a time period, e.g., the next year, has a likely drug spend in the range of between forty million dollars and sixty million dollars.

Figure 3:
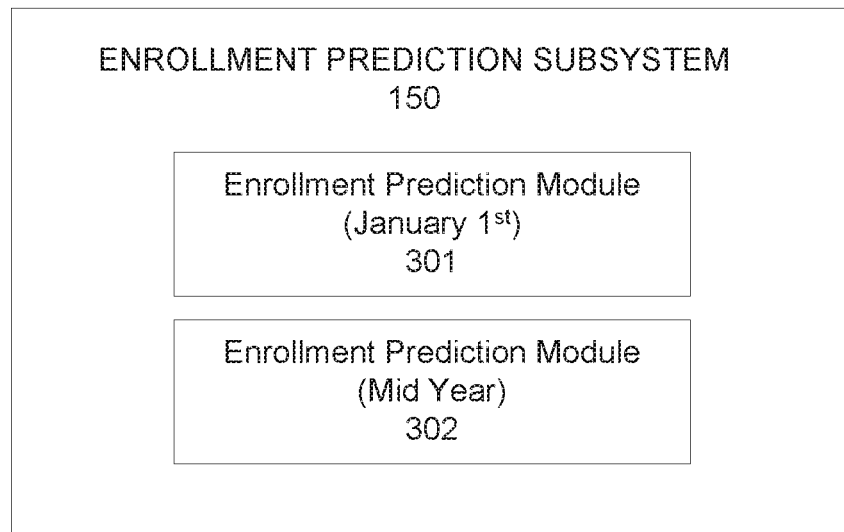
FIG. 3 is a block diagram of an example enrollment subsystem that may be deployed within the system of FIG. 1, according to an example embodiment.

FIG. 3 shows the enrollment prediction subsystem 150 may further comprise an enrollment prediction module 301 configured to process the claims data and calculate at least one set of probabilities corresponding to the likelihood that a patient will join a particular prescription drug plan and become a plan member. The enrollment prediction module 301 predicts the number of new members to the prescription plan. In an example, embodiment, the patient may be a virtual patient. A virtual patient is a statistical representation of a patient who may enroll in the program over a certain period of time. The virtual patient may be a representation of a likely patient or a very probable patient who is statistically more likely to join enroll than a likely patient. In some iterations, the virtual patient may be an unlikely patient. These different virtual patients may be represented in different models. The historical data, e.g., member data and virtual prescription drug event data, may be generated by copying the data from existing members of the plan.

In one embodiment, the demographic data associated with a randomly selected member of a plan is copied for a new member to the plan. This creates a new member to the plan having realistic demographic data.

Due to the differences between patients that join a prescription drug plan at various parts of the year, the enrollment prediction module 150 may be configured so as to provide for multiple enrollment modules. For example, FIG. 3 illustrates a first enrollment prediction module 301 that will model those patients that become plan members in January of a given year. A second enrollment prediction module 302 may be configured to model those patients that will become plan members at any other point in time throughout the year. Such a configuration ensures that the different variables, such as differences in age, associated with these different types of plan members are appropriately accounted for by the enrollment prediction subsystem 150.

Figure 4:
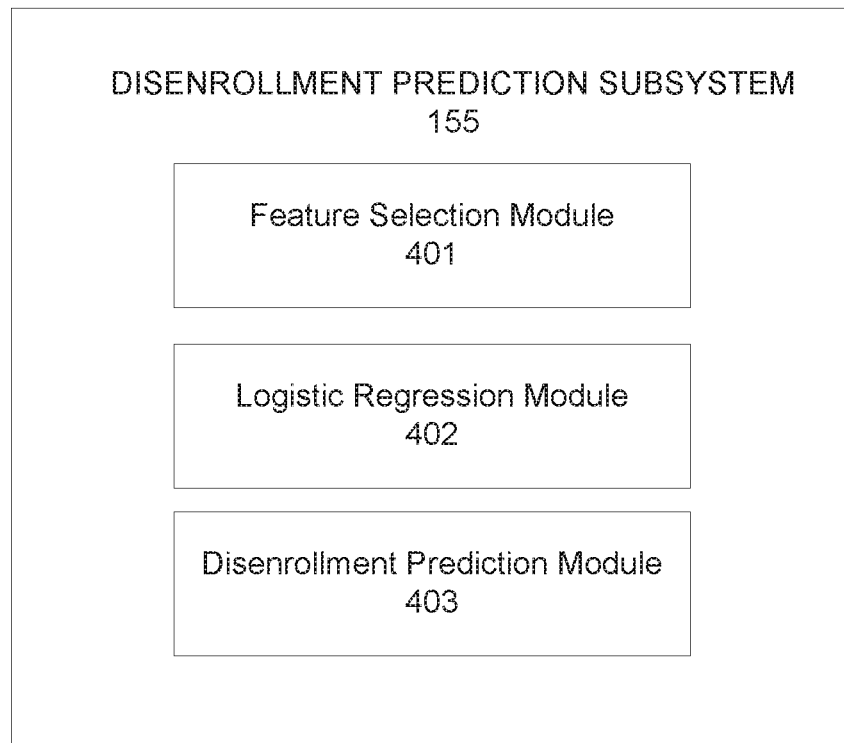
FIG. 4 is a block diagram of an example dis-enrollment subsystem that may be deployed within the system of FIG. 1, according to an example embodiment.

FIG. 4 shows the dis-enrollment prediction subsystem 155 may be configured to generate at least one set of probabilities corresponding to the likelihood that a particular plan member will leave a prescription drug plan. This prediction subsystem 155 may further comprise a feature selection module 401, a logistic regression module 402, and a dis-enrollment prediction module 403.

The feature selection module 401 may be configured to generate a first subset of claims data representing those variables that are correlated to a plan member leaving a prescription drug plan.

A logistic regression module 402 may be configured to generate at least one set of parameters for running future dis-enrollment prediction models.

After applying the feature selection techniques and linear regression model, the dis-enrollment prediction module 403 may be configured to process the claims data and calculate the set of probabilities corresponding to the likelihood that a plan member will leave the prescription drug plan.

Figure 5A:
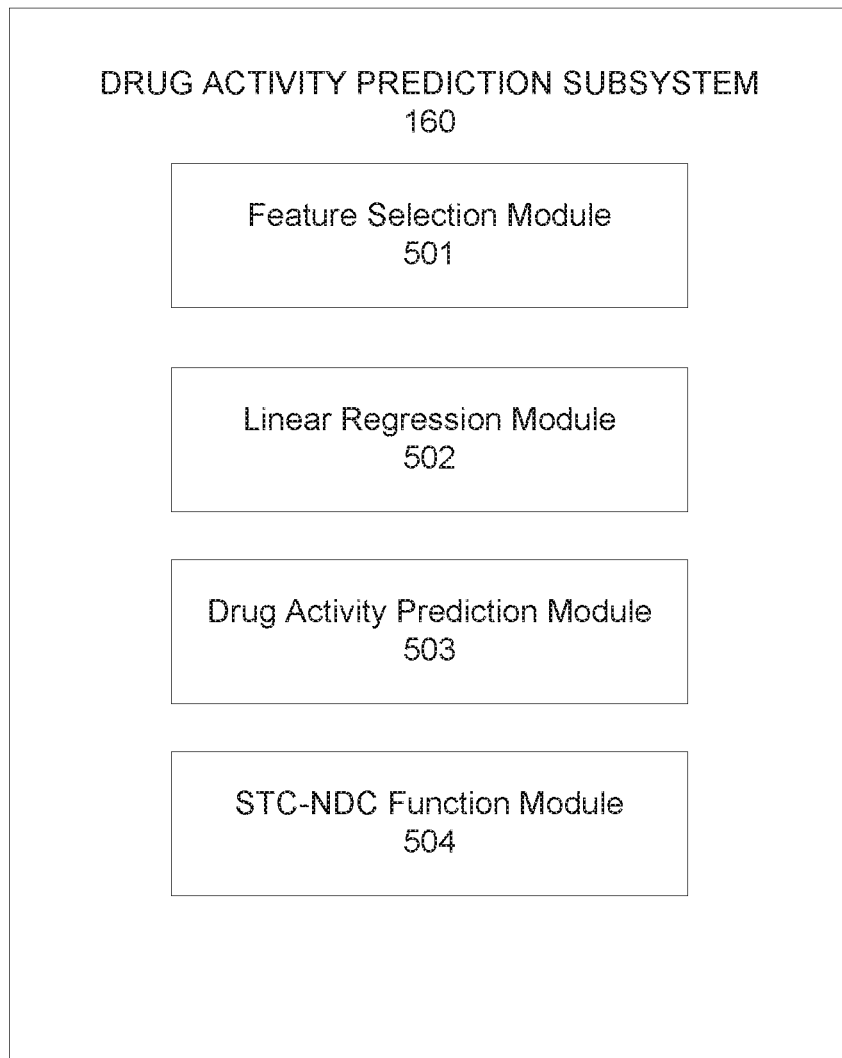
FIG. 5A is a block diagram of an example drug activity prediction subsystem that may be deployed within the system of FIG. 1, according to an example embodiment.

FIG. 5A shows a drug activity prediction subsystem 160 that may be configured to calculate at least one set of probabilities corresponding to least one of: the likelihood that a plan member will start taking a particular new drug, the likelihood that a plan member or a virtual plan member will continue or start to take a particular drug, and the likelihood that a plan member will stop taking a particular drug. This prediction subsystem 160 may further comprise a feature selection module 501, a linear regression module 502, a drug activity prediction module 503, and a STC-NDC function module 504. The feature selection module 501 and the linear regression module 502 may be configured to operate as described in connection with the dis-enrollment prediction subsection 155 but here these modules are configured to focus on those features and parameters that are correlated to drug activity probabilities rather than on those features and parameters that are correlated to dis-enrollment of a plan member. The drug activity prediction module 503 may utilize a second subset of claims data generated by the feature selection module 501 and the parameters generated by the linear regression module 502 to calculate the set of probabilities associated with drug activity. When the drug activity prediction module 503 determines that a plan member will start taking a new drug, the STC-NDC function module 504 may be selected to determine which specific new drugs the plan member will start taking. This STC-NDC function module 364 then generates a quality distribution representative of the likelihood the plan member will start taking any one of a number of new drugs.

The accounting prediction subsystem 165 may then be selected by the system 100 to predict one or more different financial outcomes of the prescription drug plan based on the probabilities generate by each predictive subsystem and the claims data.

Figure 5B:
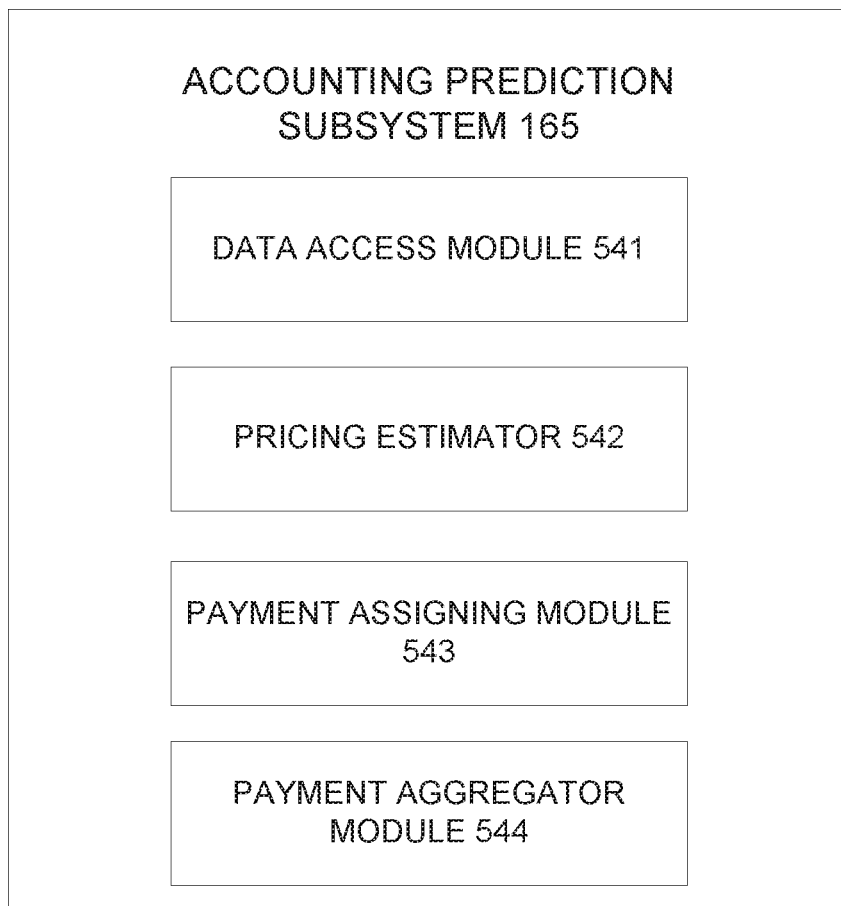
FIG. 5B is a block diagram of an example accounting subsystem that may be deployed within the system of FIG. 1, according to an example embodiment.

FIG. 5B shows an accounting prediction subsystem 165 that includes a data access module 541, a pricing estimator 542, a payment assigning module 543 and a payment aggregator module 544. Each of these elements in the data iteration subsystem 167 may include one or more than one processor and memory dedicated to performing the tasks of the respective element. The data access module 541 may interact with other data storage in the data subsystem 105. The data access module 541 can access drug pricing data (e.g., from the rebate and pricing data store 132), formulary tier data (e.g., from the formulary store 115), and drug exclusivity status of the synthetic PDE data (e.g., from the drug activity prediction subsystem 160 or data subsystem 105). The pricing estimator 542 can generate a pricing estimate for each synthetic prescription drug event of a plurality of synthetic prescription drug events. The payment assigning module 543 can assign payment responsibility for each synthetic prescription drug event in accordance with plan coverage rules based on a determination of the location in the phase of coverage.

Figure 5C:
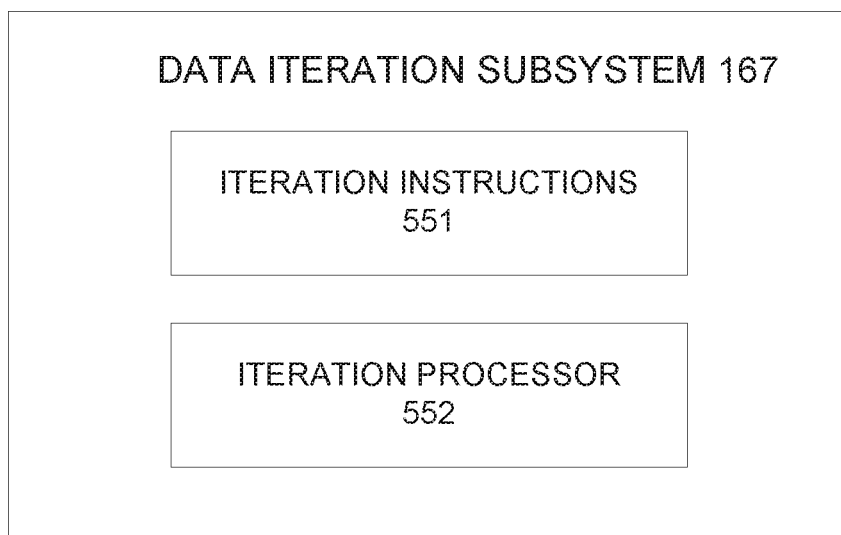
FIG. 5C is a block diagram of an example data iteration subsystem that may be deployed within the system of FIG. 1, according to an example embodiment.

FIG. 5C shows the data iteration subsystem 167 that includes machine instructions 551 to run multiple iterations of the model generation or executes the model to develop statistical results based on the model. The iteration machine instructions are processed on an iteration processor 552. In an example embodiment, the data iteration subsystem 167 repeatedly runs the model, which may be a stochastic model, to simulate potential future events.

Figure 6:
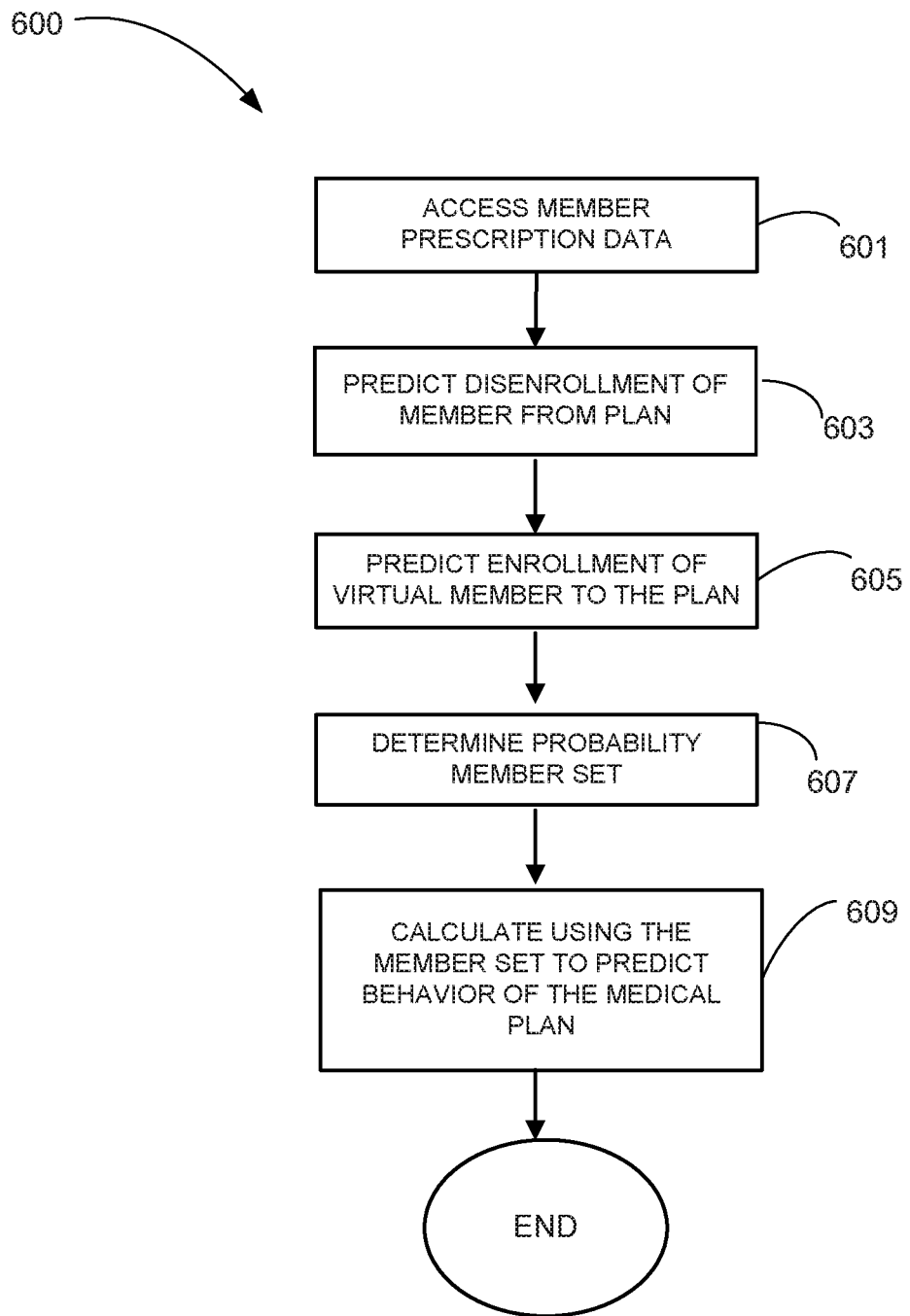
FIG. 6 is a flow chart of a method for predicting drug events, according to an example embodiment.

FIG. 6 shows a method 600 according to the present disclosure. At 601, the medical or prescription data is accessed. This data can be based on the aggregation of medical or prescription data from multiple sources. This data can provide a subset of big data that can provide meaningful results. The data can be for a specific member set of the data for a specific plan.

At block 603, a prediction is made as to whether a member will leave the specific plan. The likelihood of dis-enrollment for each member of the plan (at the member level) is calculated.

At block 605, a prediction is made as to whether a member will enroll (e.g., join) the plan and (in some embodiments) the predicted attributes of each enrolled member. The enrolled member may be a virtual member based on the historical data associated with the plan data. The predicted attributes (e.g., demographic data) of such a synthetic enrolled member can be copied from a randomly or pseudo-randomly selected actual member enrolled in the plan and/or can be based on a statistical construct of two or more randomly or pseudo-randomly selected actual members enrolled in the plan (e.g., an average or median of the demographic data of the selected members).

At block 607, a probability member set is determined. This probability member set has the dis-enrolled members removed and the virtual members added. The probability member set represents the contents of the members (both real and synthetic) in the plan based on the predictions of which real members will leave the plan in the upcoming time period and which synthetic members will join the plan in the upcoming time period.

At block 609, calculation using the probability member set is performed to predict the behavior of the member set over a time period. This can include stochastic results of various outcomes. For example, the likelihood of changes in spend, costs, drug usage and the like may be calculated in order to predict prescription drug events of the members in the probability member set.

After step block 609, the method may end. In some embodiments, the method 600 can be repeated one or more additional times. For example, the method 600 can be repeated one or more additional times with the same or different member sets.

Figure 7A:
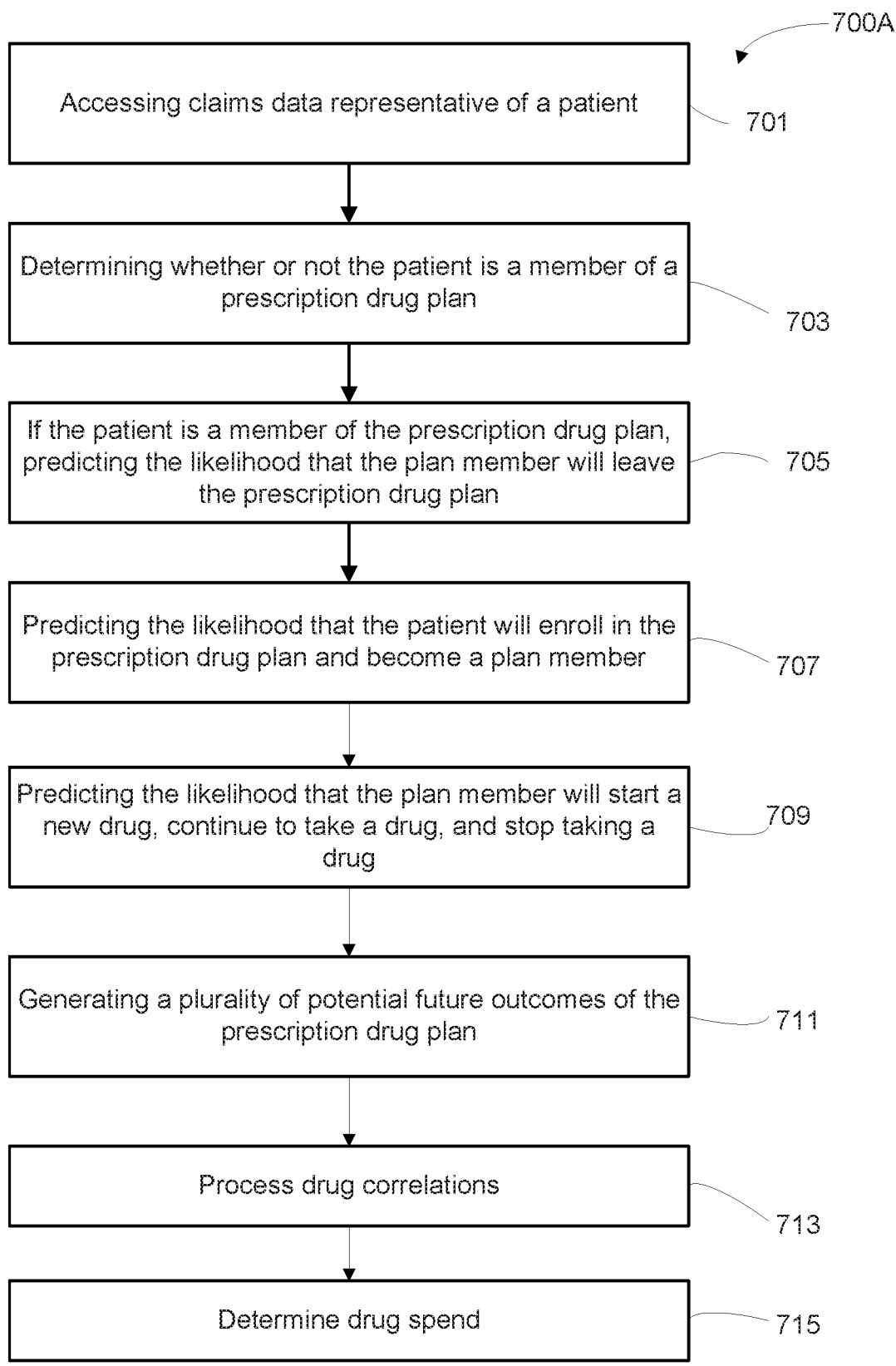
FIG. 7A is a flow chart of a method for predicting drug events, according to an example embodiment.
Figure 7B:
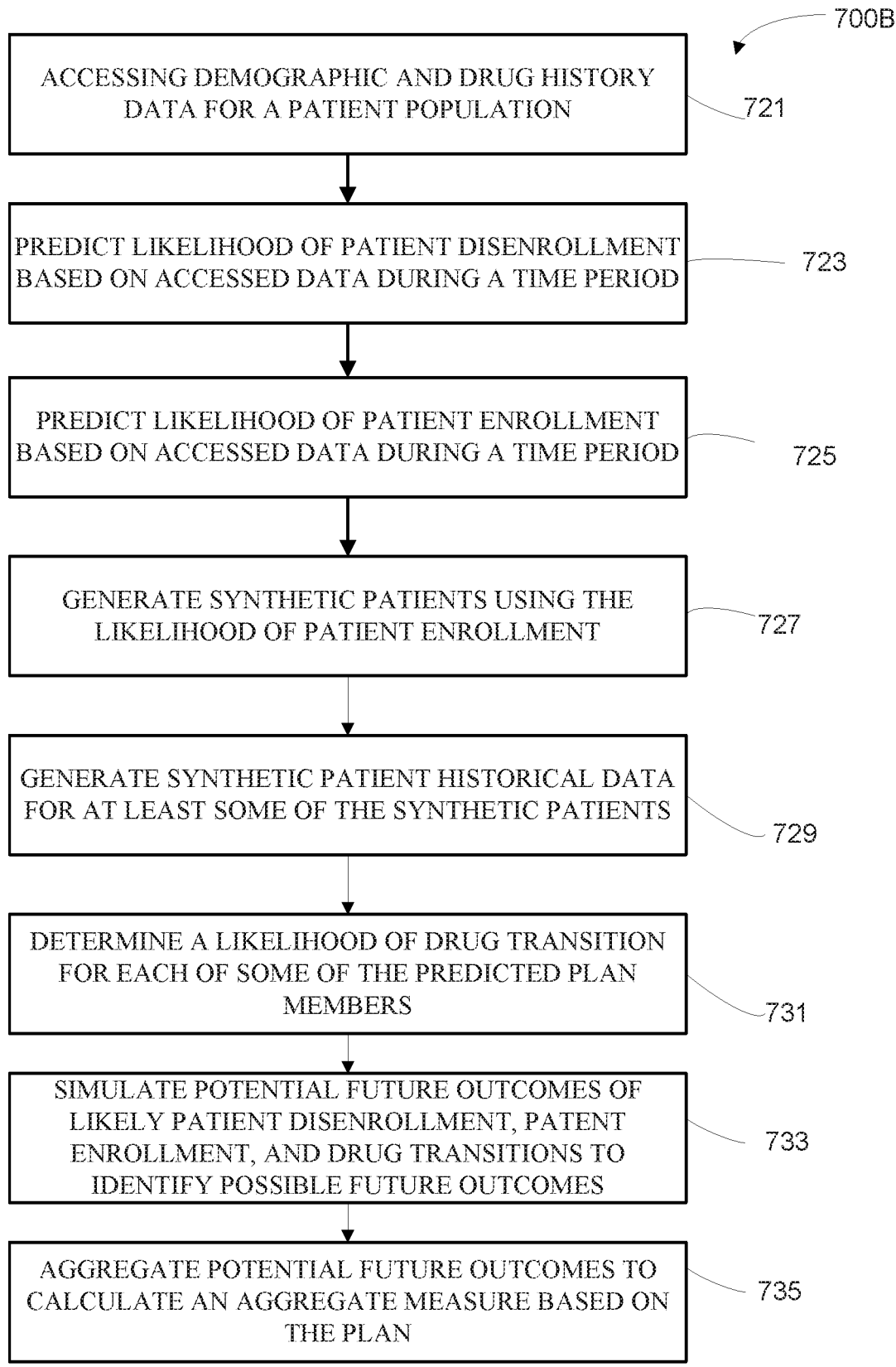
FIG. 7B is a flow chart of a method for predicting drug events, according to an example embodiment.

FIGS. 7A and 7B show methods 700A and 700B that may comprise accessing claims data representative of a patients who may or may not already be a plan member in step 701. The methods 700A, 700B may be separate methods. This claims data may be stored on a server and accessed by a processor or more than one processor, which, when executing the present disclosure, operate as dedicated machines specifically constructed to execute the operations described in the present disclosure. The present disclosure contemplates that a wide variety of different types of information may be extracted from the claims data and used as inputs to the predictive data models disclosed herein. For example, this claims data may comprise, but is not limited to: member data, a benefit plan structure, a benefit plan phase, one or more imposed drug correlations, an applicable formulary, a drug correlation matrix, price data, cost data and prescription drug data. Member data may comprise a member identification number, which is a number is used to track plan members without exposing personally identifiable health information, and other demographic information such as age, age percentile relative to the entire prescription drug plan population, a risk score provided by the Centers for Medicare & Medicaid Services, a risk score percentile relative to the entire prescription drug plan population, gender, state and zip code of residence, which prescription drug plan product the plan member is subscribed to, and whether or not the plan member qualifies for low income status as defined by guidelines of the Centers for Medicare & Medicaid Services.

Prescription drug event data may comprise the member identification number and more detailed information about each prescription drug the plan member is or has taken including each applicable Specific Therapeutic Class Code ("STC Code") and National Drug Code ("NDC") for each drug. The National Drug Code also includes information related to the drug's dosage, quantity, and manufacturer. It is important to note that there may be multiple National Drug Codes for each drug, representing different doses, packaging, and other variables and the method 700 may extract all of the relevant National Drug Codes.

Referring again to FIG. 7A, once the claims data has been accessed in block 701, at 703, it is determined whether or not the patient is plan member.

At block 705, if the patient is a plan member, a dis-enrollment prediction subsystem may use the claims data to calculate at least one set of probabilities corresponding to the likelihood that such plan member will leave the prescription drug plan. The claims data may represent the historical probability that a plan member with similar characteristics will leave a similar prescription plan.

At block 707, an enrollment prediction subsystem may use the claims data to calculate at least one set of probabilities corresponding to the likelihood that a patient will join the prescription drug plan and become a plan member. The plan members that are predicted to be in enroll in the plan may be virtual or synthetic members that include predicted actions in the plan. These newly enrolled virtual plan members may be added to the enrollment model population. The number of new members, demographic information, and drug histories of these new plan members may be modeled based on historical data. In practice, prescription drug plans typically observe a large number of new plan members in January of each year, following an open enrollment period in the previous November. Prescription drug plans also observe a steady trickle of new plan members throughout the rest of the year, largely as people age into the Medicare benefit. It will be recognized that other plan years may be used resulting in some plans seeing an increase at months other than January for these plans. These populations are quite distinct and may be modeled separately in an embodiment of the method 700. In each simulated month, the enrollment prediction subsystem may add a number of new members chosen from a Gaussian distribution with mean and standard deviation calculated based on the historical observations from the calendar month being simulated, and scaled to the size of the simulated population. For example, if the enrollment model is simulating 10% of the total prescription drug plan membership, the new plan member additions will be divided by 10. Each newly added plan member in a modeled instance may be selected from historical data. For example, if the enrollment model is adding a plan member in January, the model will randomly select a real plan member who joined in a previous January, and their demographic and drug information is copied into the model as a new plan member. The model may also base the new member of composites of prior members from the historical data.

Claims data contains a large amount of information with a large number of different data features. When a data set comprises a large number of features, feature selection techniques can be applied to generate a subset of those features that are most relevant to the data being processed or the solution to be solved. Examples of feature selection techniques contemplated by the present disclosure include, but are not limited to, Least Absolute Shrinkage and Selection Operator ("LASSO"), ridge regression, simulated annealing, best-first search, a genetic algorithm, greedy forward selection, greedy backward elimination, exhaustive, particle swarm optimization, targeted projection pursuit, scatter search, and variable neighborhood search.

Models employing feature selection provide for several advantages over models that do not. Perhaps the most important advantage is that feature selection reduces overfitting of training data. Models that have been overfit have poor predictive performance because the model describes error and noise rather than the parameters evaluated. Other advantages include simplifying calculations and shortening training times for the models.

In the method 700 of the present disclosure, feature selection may be applied when generating dis-enrollment probabilities of block 707. In such an embodiment, a first subset of claims data, which is representative of those variables that are highly correlated to a plan member leaving a prescription drug plan, may be generated using one or more feature selection techniques. At least one set of parameters may then be saved to a server for running future dis-enrollment prediction models. These parameters may be generated by utilizing one or more algorithmic techniques such as linear regression.

At block 709, the method includes predicting, using a drug activity prediction subsystem and the claims data at least one of the following: the likelihood that the plan member will start taking a particular drug, the likelihood that a plan member will continue to take a particular drug, and the likelihood that a plan member will stop taking a particular drug. The feature selection and algorithmic techniques described with reference to step 707 may also be applied at 709. In such an embodiment, a drug correlation matrix may be generated at the Specific Therapeutic Class code level. Here, a binary matrix is generated so that if the plan member is taking a specific drug in an Specific Therapeutic Class code, the plan member is assigned a 1. If the plan member is not taking the specific drug in the Specific Therapeutic Class code, then the plan member is assigned a 0. A feature selection technique may then choose the variables for predicting drug activity and generate a second subset of the claims data that is correlated to these variables. At least one algorithmic technique, such as linear regression, may be applied to this second subset of claims data to generate at least one set of parameters for running the drug activity prediction model and these parameters may be saved to a server for future runs of the model.

The drug activity probabilities may be calculated for specific periods of time. As described above, the system and method of the present disclosure provide for building data prediction models on a monthly basis and then rolling each of these monthly results into the full year. Drug predictions are performed at the level of Specific Therapeutic Class codes. That is, for each Specific Therapeutic Class code, the method 700 can determine the odds of a plan member stopping or starting at least one drug within that Specific Therapeutic Class code. If the method 700 decides that a plan member will start a medication associated with a new Specific Therapeutic Class code, then the method may further utilize a function that converts the information into National Drug Code information (this function may be referred to herein as an "STC-NDC function"). Such a conversion enables the method 700 to determine the number of new prescriptions and the specific chemical, dose, and price of these new drugs. While the present disclosure focuses on predictions based on the level of Specific Therapeutic Class codes, the present disclosure also contemplates that predictions could also be done at the level of National Drug Codes, Hierarchical Ingredient Codes ("HICs"), Generic Code Numbers ("GCNs"), Main Clinical Indicators ("MCIs"), or Competitive Product Categories ("CPCs").

When the method 700A determines that a plan member will start taking a drug with a new National Drug Code, the STC-NDC function predicts which specific new drug(s) that plan member will start taking. The STC-NDC function may be first trained on historical data, where the drug activity model looks at all plan members who are taking at least one drug in a given Specific Therapeutic Class code. The model may then calculate the quantity distribution and the relative frequency of each National Drug Code within this Specific Therapeutic Class code. This means that the model will evaluate the probability that, if a plan member is taking at least one drug in this Specific Therapeutic Class code, they will be taking a second, third, etc. drug. For example, a plan member assigned a new Specific Therapeutic Class code might have a 90% chance of taking another drug, a 7% chance of taking two other drugs, and a 3% chance of taking three other drugs, etc. After determining the number of new drugs, the National Drug Codes of these drugs are determined. A plan member assigned one new National Drug Code might have a 50% chance of being prescribed a medication assigned a National Drug Code A, 30% chance of being prescribed a medication assigned a National Drug Code B, 15% chance of being prescribed a medication assigned a National Drug Code C, and 5% chance of being prescribed a medication assigned a National Drug Code D. This STC-NDC function also optionally assigns a price to each prescription drug event based on the historical average for that National Drug Code, modified (e.g., increased or decreased) by an inflation factor specified for brand-name or generic drugs.

At block 711, one or more distributions of potential future outcomes of the prescription drug plan are generated by running at least one stochastic model utilizing the plurality of probabilities generated by each of the prediction subsystems described above. Each iteration of the stochastic model generates synthetic claims data which is then displayed as distributions in the form of a histogram (or in another form), although the present disclosure contemplates that other statistical techniques may be used to display these or other outcomes as well. The stochastic model resolves the probabilities generated by each prediction subsystem and may be configured to resolve these probabilities to thereby simulate each month in a year of a prescription drug plan (or to simulate other time periods within another, different longer time period).

The stochastic model may be run any number of times to generate a distribution of predicted future outcomes, based on this synthetic claims data, representative different scenarios the prescription drug plan may experience. For example, to simulate month one (1) for the year, the stochastic model will generate a plurality of probabilities to determine which plan members will drop out of the prescription drug plan, which synthetic members will join the plan, and which medications the plan members will start or stop taking. The probabilities that are generated may then be rolled forward to month two (2) of the prescription drug plan year and the stochastic model is run again. For example, another stochastic iteration of the model may be performed, but using the member data and synthetic member data determined for the first month. This process may be repeated until the simulation reaches the final month of the year, at which point the outputs are stored.

At block 713, the method may process one or more drug correlations based on a new drug the plan member has been prescribed or a new diagnosis the plan member receives. This processed correlation overcomes the limitations of the prior art by considering that, in the real-world consideration, a patient is often prescribed more than one prescription drug to treat a disease or condition. The method 700 may utilize linear algebra or other algorithmic techniques to ensure the correlation in new drug prescriptions considers this correlation and matches real historical data. Without this correlation, embodiments of the method 700 would treat each drug independently, which is not accurate. Such an approach is advantageous over methods of the prior art, such as a market basket approach, which do not accurately reflect these real-world correlations.

At block 715, the method may assign drug spend to the prescription drug plan as a whole or focusing this analysis on drug spend for a particular plan member, manufacturer, or Centers for Medicare & Medicaid Services, by taking into consideration the applicable benefit structure and phase of coverage for each individual. This drug spend may be calculated by selecting an accounting prediction subsystem and utilizing the accounting prediction subsystem and the probabilities calculated by each of the predictive subsystems described above to predict one or more financial outcomes representative of the prescription drug plan or plan member. This accounting function takes the prices, formulary tiers, and the generic or brand status of particular drugs determined by the synthetic predicted drug events generated from each iteration of the stochastic model to assign a drug spend. This granular level of analysis is possible because the method 700A and 700B processes claims data and generates predictive probabilities at the individual plan member level. This level of analysis and accuracy is not possible using methods that rely on aggregate plan member data.

A random seed used to generate each iteration of the stochastic model may be stored so that various simulations of interest can later be identified. For example, one simulation of interest may be the simulation which produced the median prediction for drug spend of the prescription drug plan. Others may include the best and worst-case scenarios for the prescription drug plan for a future year or future quarter. This specific iteration can be re-run using the stored random seed so that the model will produce the exact same result as the specific iteration did during the initial iteration. Detailed information may be stored from that model, including all membership changes and prescription drug event records. Such an approach overcomes current limitations in the art because storing this information for each iteration would be space-prohibitive and cause significant delays in processing time.

Referring to FIG. 7B, the predictive model method 700B is shown.

At block 721, demographic data and drug history data for a plurality of patients of a patient population are accessed. The plurality of patients is enrolled in a plan during a selected time period. The patient population used for defining data can be from a selection of a patient population from the plan. The selection can be an entire population of the plan in an example embodiment. The selection can be a targeted population of the plan in an example embodiment. The selection can be a random or pseudorandom subset of the plan. The plurality of patients of a patient population from the plan is based on the selection of the patient population.

At block 723, a likelihood of patient dis-enrollment for each of at least some of the plurality of patients of the patient population from the plan is predicted for a time period based on the demographic data and the drug history data (e.g., the historical data). The simulation can utilize a logistic regression function to predict a likelihood of patient dis-enrollment for each of at least some of the plurality of patients of the patient population from the plan during the time period based on the demographic data and the drug history data. With this likelihood of dis-enrollment in a predictive model, the predictive model determines if any individual member will dis-enroll from the prescription drug plan.

At block 725, a likelihood of new patient enrollment into the plan during a corresponding time period to the time period is generated. This likelihood may be based on the demographic data (e.g., member data) and the drug history data (e.g., prescription drug event data and/or historical data).

At block 727, a plurality of synthetic patients based on a prediction of the likelihood of new patient enrollment into the plan is generated. This prediction may be a prediction of which synthetic patients will join the plan during the corresponding time period.

At block 729, synthetic patient historic data for each of at least some of the plurality of synthetic patients is generated. The synthetic patient historic data can include synthetic prescription drug event data, synthetic demographic data, and synthetic drug history data. This synthetic data can be the same as actual data for actual patients but is based on the probability of the synthetic patient. This synthetic data is not actual data that is used in real monies changing hands, but is a statistical representation of a fictitious patient.

At block 731, a likelihood of drug transition for each of at least some of a plurality of predicted plan members is determined (e.g., real members and synthetic members where applicable). The plurality of predicted plan members (e.g., virtual patients in the plan for the time period) may include a plurality of remaining patients from among the plurality of patients and the plurality of synthetic patients. The likelihood of drug transition can, in various example embodiments, include a likelihood of drug discontinuation being determined for each drug of at least some of a single prescription drug or a plurality of prescription drugs associated with a predictive plan member of the plurality of predictive plan members for a pharmaceutical grouping and a likelihood of drug therapy initiation with a predictive plan member of the plurality of predictive plan members for the pharmaceutical grouping. The pharmaceutical grouping can be organized in accordance with a specific therapy class level.

The drug history data can be queried to determine, for at least some of the plurality of patients taking a drug within a particular pharmaceutical grouping among a plurality of pharmaceutical groupings, a number of discrete National Drug Codes with the particular pharmaceutical grouping that the at least some of the plurality of patients has filled a prescription to create a distribution of National Drug Code usage within the particular pharmaceutical grouping.

At block 733, a plurality of potential future outcomes of the likelihood of patient dis-enrollment, the likelihood of new patient enrollment, and the likelihood of drug transition are simulated in accordance with a stochastic framework to identify a range of possible plan future outcomes are generated. The generation can be output by running various simulations of events on the data using the virtual patients and related data. The future outcomes reflect, for each of at least some of the plurality of predicted plan members, prescription drug utilization and prescription drug pricing associated with the prescription drug utilization. The simulation of the plurality of potential future outcomes includes simulation of a National Drug Code selection from the distribution of National Drug Code usage. The prescription drug utilization and the prescription drug pricing is based on the simulation of the National Drug Code selection.

At block 735, at least a portion of the plurality of potential future outcomes to calculate an aggregate measure based on the plan are aggregated. The aggregation of the outcomes provides the distributions of the results, which can be visualized, to predict the likelihood of the plan performance. Examples of the outcome include distributions of potential drug spend, net margins and the like. In one embodiment, the plan is modified based on the aggregate measure that is determined. For example, the premiums and/or co-pays charged to members in the plan can be increased or decreased based on the aggregate measure (e.g., to reduce the cost per member and/or increase the margin for the entity providing the plan), the enrollment criteria for the plan can be changed to cover more or fewer members within the plan, the formulary of medications covered in the plan (and the associated co-pays and/or deductibles) can be modified to reduce the member cost and/or increase the provider margin, or the like.

The logistic regression function to train the simulation, e.g., models, can use one or more of historical demographic data of the plan, historical drug history data of the plan, a plurality of individual level aggregate historical time period total drug spend, a plurality of individual level aggregate historical time period net insurance margins, and a plurality of individual legal aggregate historical time period total number of prescription drug events. The logistic regression function can be trained on a plurality of training set patients. The training set patient of a plurality of training set patients can be associated with an individual level aggregate historical time period total drug spend of the plurality of aggregate historical time period total drug spend, an individual level aggregate historical time period net insurance margins of the plurality of individual level aggregate historical time period net insurance margins, and an individual legal aggregate historical time period total number of prescription drug events of the plurality of individual legal aggregate historical time period total number of prescription drug events, in various example embodiments.

The training of the logistic regression function further uses a benefit plan structure of the plan, a plurality of individual level benefit plan phases, and a formulary associated with the plan, the training set patient being further associated with an individual level benefit plan phase of the plurality of individual level benefit plan phases in various example embodiments.

When transforming historic prescription drug event data from the drug history data into a pharmaceutical grouping organized data structure for at least some of each of the plurality of patients, a patient of the plurality of patients is positioned in the data structure with either a first indication in a position within the pharmaceutical grouping organized data structure to reflect that a drug or a second indication in the position within the pharmaceutical grouping organized data structure to reflect that the drug is not being taken. The feature selection algorithm is applied to the pharmaceutical grouping organized data structure to select a plurality of inputs. The utilization of the logistic regression function to predict the likelihood of patient dis-enrollment is based on input of a portion of the demographic data, the drug history data, or both the demographic data and the drug history data identified by the plurality of inputs.

The pharmaceutical grouping organized data structure is a binary matrix in an example embodiment.

The drug includes a grouping of drugs in accordance with a Specific Therapeutic Class code in an example embodiment. The pharmaceutical grouping organized data structure can be organized by Specific Therapeutic Class codes.

The drug can include a grouping of drugs in accordance with a National Drug Code or Main Clinical Indicator.

The feature selection algorithm can include Least Absolute Shrinkage and Selection Operator, ridge regression, simulated annealing, best-first search, a genetic algorithm, greedy forward selection, greedy backward elimination, exhaustive, particle swarm optimization, targeted projection pursuit, scatter search, variable neighborhood search, or combinations thereof.

The simulating of the plurality of potential future outcomes can include determining a historical patient-wise covariance between utilization of different pharmaceutical groups based on the drug history data. The covariance data 130 can be stored in the database 105. The covariance data 130 can be in the form of matrices representing joint variability of the variables in the healthcare data.

The simulating of the plurality of potential future outcomes can include utilizing linear algebra techniques to impose the historical patient-wise covariance during application of a stochastic model.

The utilizing linear algebra techniques can include generating a matrix of binomial distributions with specified covariance; and applying a threshold value to the matrix to resolve each number in a binomial distribution within the binomial distributions to a first indication or a second indication. The threshold value is determined by a logistic regression function in an example embodiment.

The methods described herein may include accessing drug pricing data, formulary tier data, and drug exclusivity status of the synthetic prescription drug event data. A pricing estimate for each synthetic prescription drug event of a plurality of synthetic prescription drug event is generated. A location in a phase of coverage of the plan for each of at least some of the plurality of patients is determined. Payment responsibility for each synthetic prescription drug event in accordance with plan coverage rules based on a determination of the location in the phase of coverage is assigned. Payment information for a patient, the plan, a drug manufacturer, a responsible governmental organization, or combinations thereof is aggregated. These can be used in the simulation in methods 700A or 700B.

In the methods described herein, the time period is within about the next month, and wherein the corresponding time period is for a same period of time.

In the methods described herein, the prediction of the likelihood of patient dis-enrollment can include predicting the likelihood of patient dis-enrollment for each of at least some of the plurality of patients of the patient population from the plan during the time period based on the demographic data, the drug history data, and health data for at least some of the plurality of patients.

In the methods described herein, the aggregate measure based on the plan includes overall plan performance.

In another embodiment, the present disclosure provides for a non-transitory machine readable medium comprising machine executable instructions, where, when executed by one or more processors, causes the processors to perform a set of operations. These instructions may include any of the steps of algorithms 700A and/or 700B and/or may be written by a person of ordinary skill in the art based on the algorithms 700A and/or 700B. These instructions may instruct the processors to perform operations including accessing claims data representative of a patient and determining whether or not the patient is a plan member. If the patient is a plan member, the instructions may instruct the processors to calculate a set of probabilities corresponding to the likelihood that the plan member will leave the prescription drug plan. If the patient is not a plan member, the instructions may instruct the processors to calculate a set of probabilities corresponding to the likelihood that the patient will enroll in the prescription drug plan and become a plan member. The instructions may further direct the processors to calculate at least one set of drug activity probabilities representative of at least one of: the likelihood that a plan member will start taking a new drug, continue taking a drug, or stop taking a drug. The instructions may then direct the processors to generate distributions of potential future outcomes of the prescription drug plan under a variety of different potential circumstances.

In an embodiment, the non-transitory machine-readable medium includes machine-readable instructions that, when executed by one or more processors, may further direct the processors to generate one or more sets of synthetic claims data representative of one or more plan member for each iteration of the stochastic model. In another embodiment, the non-transitory machine-readable medium includes machine-readable instructions that, when executed by one or more processors, may further direct the one or more processors to generate one or more predictive financial outcomes representative of the prescription drug plan for each iteration of the stochastic model.

Figure 8:
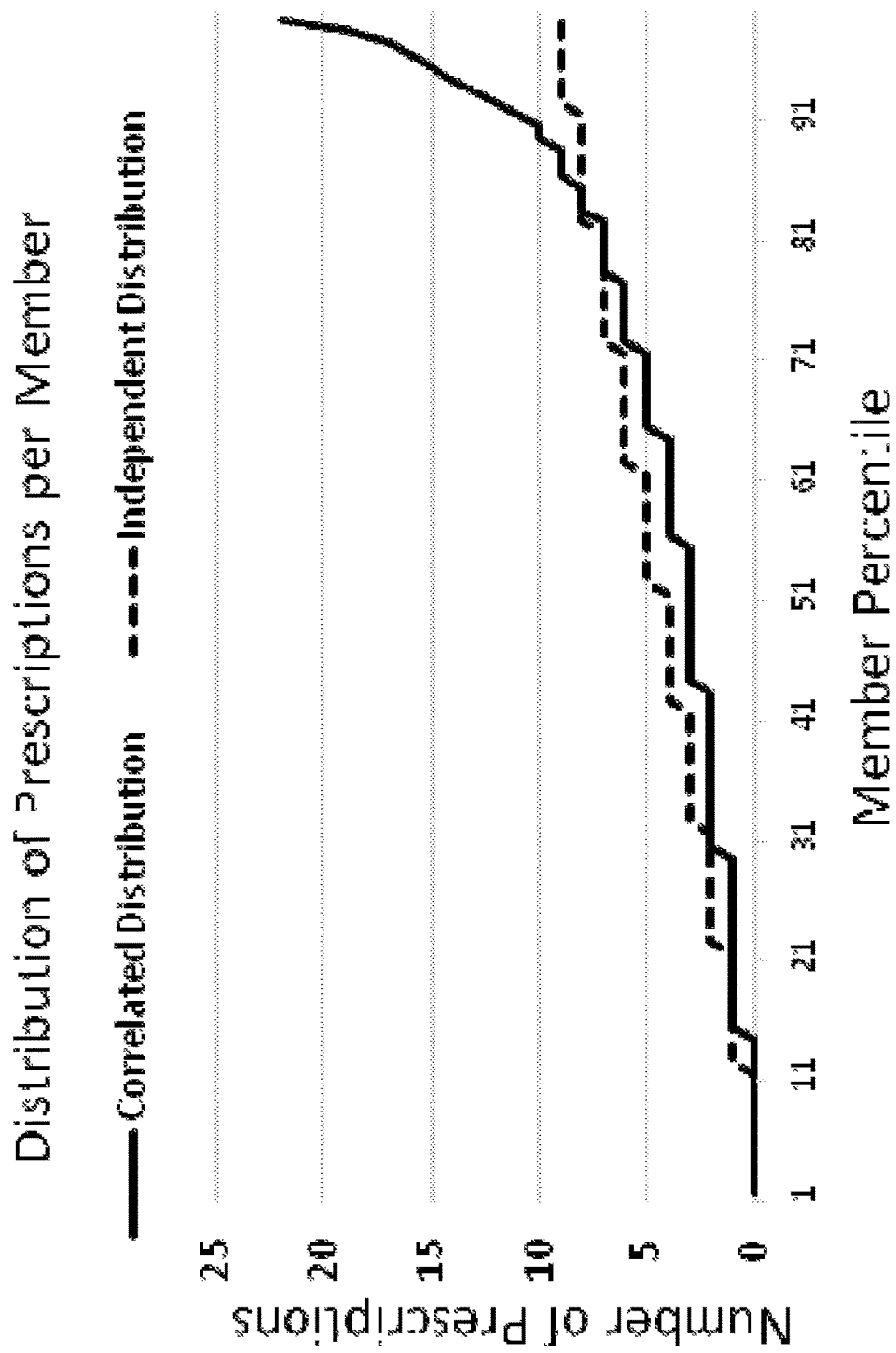
FIG. 8 is a graphical illustration of the differences in forecasting outcomes using a correlated drug distribution and an independent drug distribution, according to an example embodiment.

FIG. 8 shows a graph 800 imposing this drug correlation. The data may be at least part of the covariance data 130. The graph 800 may be output by a processor accessing the data from a memory. The processor outputs instructions to control a display screen to show the graph. Here, the number of prescriptions for a plan member is correlated by the percentile of the prescription drug plan membership. The results are dramatically different when these drug correlations are imposed as compared to when the drug correlations are not. A method that does not impose these drug correlations would may lead to inaccurate forecasting of drug spend for the prescription drug plan as a whole or forecasting on the plan member level, in some example embodiments.

In an embodiment, these imposed drug correlations may be achieved using a binned data (e.g., bindata) software package, which may identify or use binned predictor variables. For example, the software may be bindata package for R. However, this software has an original run time of approximately fifteen minutes, which is prohibitively slow. The package also may not be calibrated properly to the low probabilities and low imposed drug correlations that may be used by the system and method disclosed herein. To overcome these limitations, the executable code used to run the various predictive subsystems and stochastic model may be translated into C++ to provide for faster run times. A search function in the bindata package may also be replaced with a lookup table to increase the speed of run times. This lookup table may further be configured to store values that are compatible with the low probabilities which are frequently used by the method.

Figure 9:
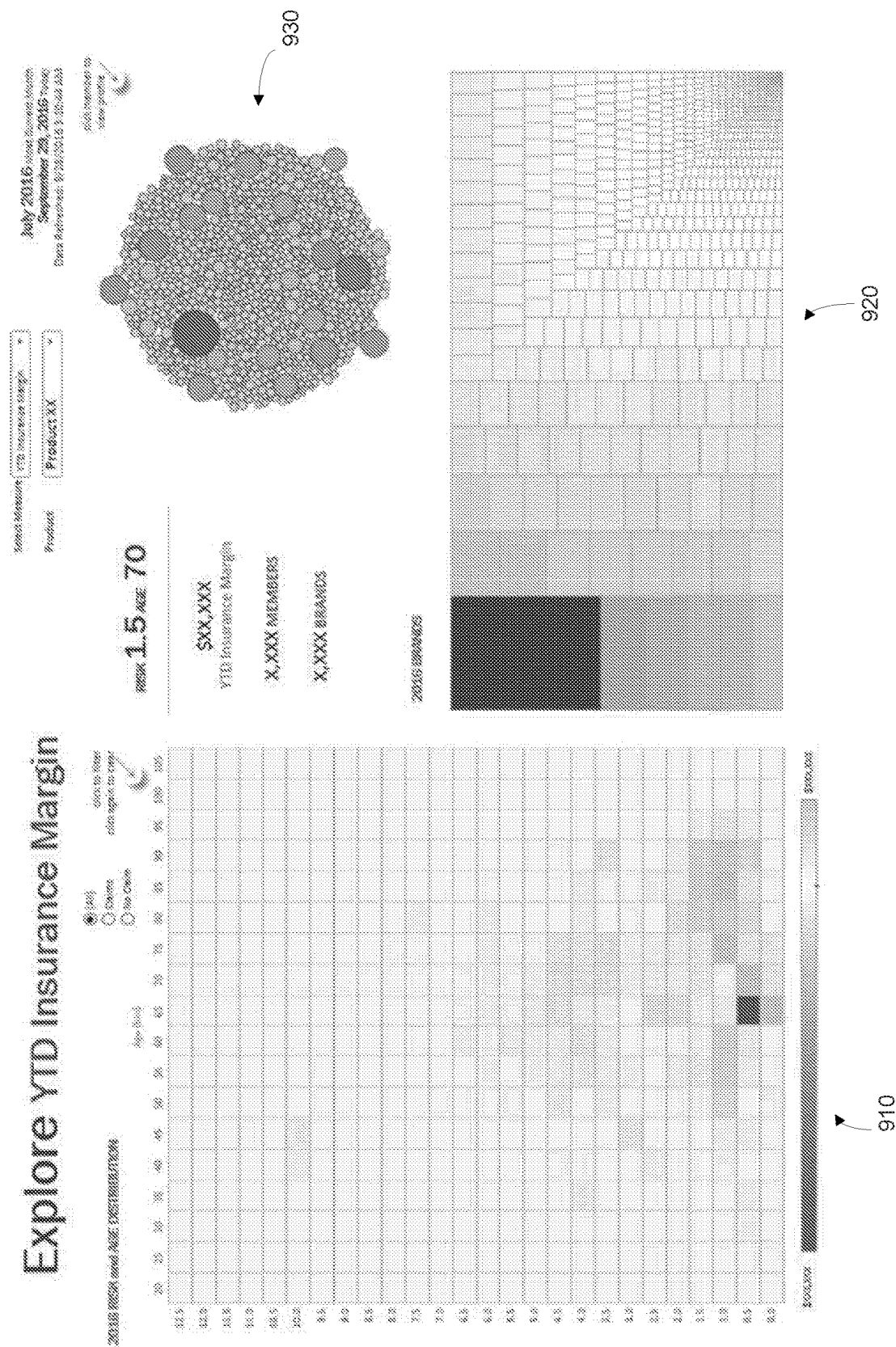
FIG. 9 is a graphical illustration of various visualizations that may be created, transmitted and/or displayed using the system and method of the present disclosure, according to an example embodiment.
Figure 10:
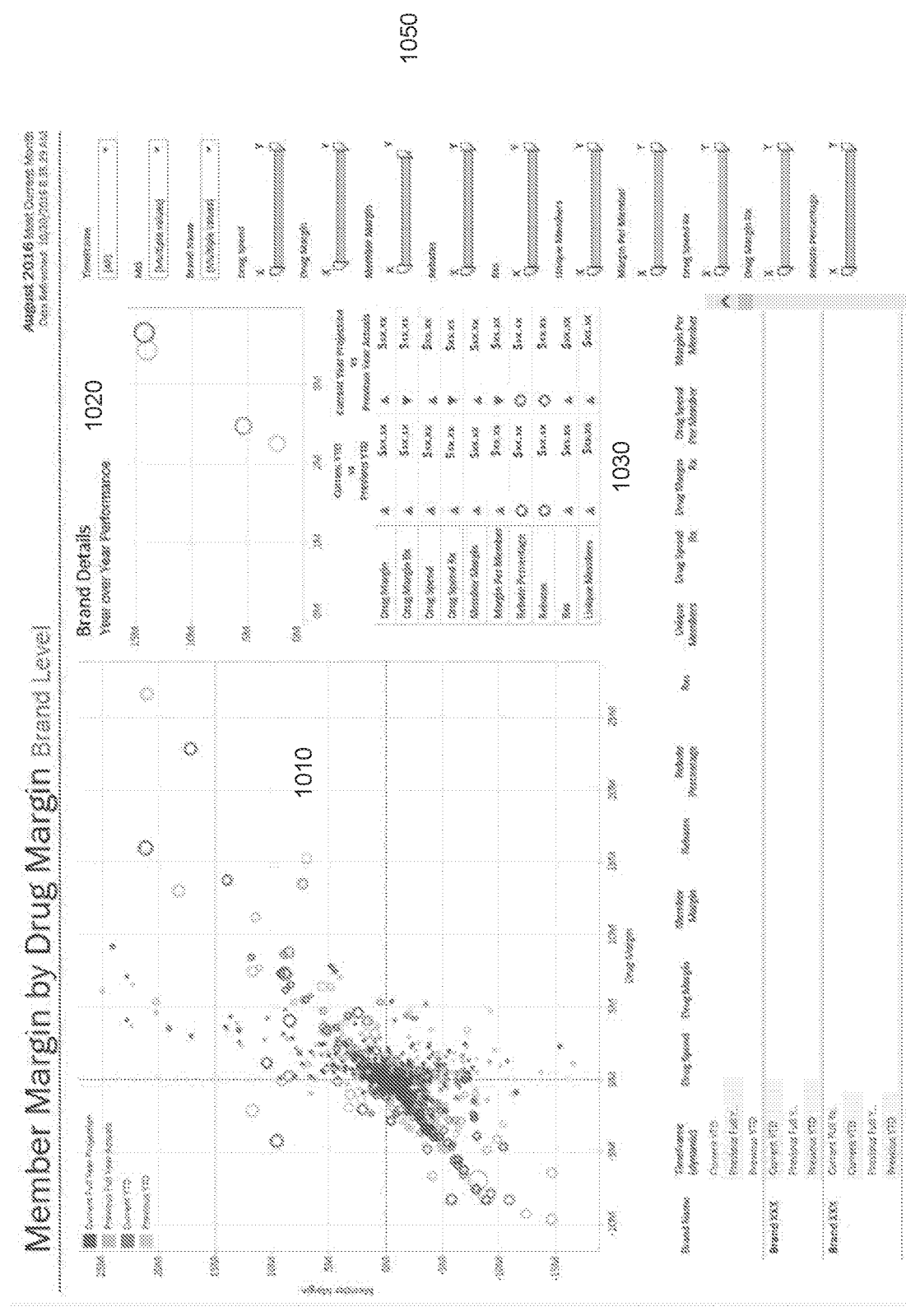
FIG. 10 is a graphical illustration of various visualizations that may be created, transmitted and/or displayed using the system and method of the present disclosure, according to an example embodiment.

FIG. 9 and FIG. 10 relate, respectively, to exemplary visualizations 900, 1000 that can be generated using the system and method disclosed herein. Such visualization tools may be provided in the system 100 provide for detailed, interactive displays of the results of analyzing claim data using the system and method of the present disclosure, which may be remote from the processors and servers. These visualizations 900, 1000 may be highly customized to display that information which is most relevant to a particular business issue being evaluated by a user and may range from total drug spend of the prescription drug plan as a whole to individual prescription drug event or other claims data for a specific plan member or a subset of members. The benefits of accessing claims data at the individual plan member level are highlighted by these visualizations, which provide snapshots of particular points in time in which forecasted data generated based on synthetic claims data generated using the system and method disclosed herein is equally as detailed as historical real data.

Referring to FIG. 9, it shows various visualization parts of prescription drug plan data processed using the system and method disclosed herein. Various visualization features 910, 920, and 930 may be displayed and manipulated by a user to extract information and make informed business decisions based on forecasted data produced according to the present processes and systems. These visualizations are flexible enough to enable a user to assess information at the level of each plan member while being robust enough to provide the information needed to evaluate the prescription drug plan as a whole. As can be seen in FIG. 9, any number of features may be added and customized to provide for visualization of that data which is of interest, e.g., by drafting queries to the data, processing the data for visual display, and transmitting the processed data for display on an electronic device, e.g., a mobile display.

The visualization feature 910 is a heat map graph showing insurance margin for a plan over a time period, e.g., year-to-date or annual, as a function of risk and age distribution in the plan with each intersecting area of risk and age showing a probable insurance margin. For example, a risk and age distribution 910 may be generated, which assigns a risk score to each plan member based on the results of the predictive modeling and forecasting methods and displays this risk score as a function of each plan member's age. Each square of this distribution 910 represents a particular member population. Such a visualization therefore provides a user with detailed information about a particular population of the prescription drug plan as this information relates to insurance spend across various drugs. The visualization feature 920 is a tree map graph showing hierarchical data using nested rectangles. The rectangles show different drug brands for the time period being processed. Details relating to specific prescription drug manufacturers can be also be displayed 920 using a graphical representation to provide a user with an easily understandable snapshot of information related to the number of prescriptions associated with each manufacturer assigned to plan members and therefore associated with the prescription drug plan. The visualization feature 930 is an occurrence map showing the members with a risk score of 1.5 and an age of 70. The time period for the visualizations can be a future time period that includes simulated enrollees and predicted enrollees into the plan as described herein. Each plan member may also be graphically represented in display portion 930 in a manner that not only provides a user with an overall perspective of the total plan members but also provides for the flexibility for a user to analyze each plan member at an individual level by selecting those plan members that are displayed as having high or low total drug spend.

FIG. 10 provides an additional exemplary visualization 1000 that may be generated in electronic devices using software instructions, e.g., using Tableau® software and data processed using the system and method disclosed herein. Here, data is displayed in terms of drug to plan member margins. The drug margin can be displayed in display portion 1010 as both historical real data and forecasted out to specific points in time in the future using synthetic data. In this display portion 1010, each drug is represented by four circles corresponding to the current year projection, the previous year actual, the current year to data ("YTD"), and the previous YTD. More detailed information may also be displayed as set forth in display portion 1020 and display portion 1030 to provide summaries of a specific drug brand's performance over time and the specific drug spend per plan member considering factors such as rebates and drug margin. A number of parameters are shown in display portion 1050 and may be configured to customize the displays with respect to a particular timeframe, drug brand, or drug spend.

As illustrated by the visualizations of FIG. 9 and FIG. 10, the system and method disclosed herein provide a powerful tool that can be used to address a variety of different business issues and concerns. In an application, the system and method of the present disclosure may be used for formulary optimization. The business issue addressed is, if a drug manufacturer offers a rebate on a particular drug, whether or not a pharmacy benefit manager should add the particular drug to its formulary. Using current actuarial methods, which are based on aggregate data, the drug would appear to provide a positive financial outcome when considering the rebate and therefore should be added to the formulary. However, the financial impact from the type of plan member that would take this particular drug is unknown. By calculating the future plan member level profitability and utilization of the type of plan member that is attracted to the particular drug, the pharmacy benefit manager can determine if the aggregated drug basket of these plan members will have a negative financial impact on the prescription drug plan. Often, when the system and method of the present disclosure are applied, which evaluates such questions using claims data accessed on the individual plan member level, the determination is very different. In this use case, a pharmacy benefit manager can avoid adding a particular drug to the formulary when traditional actuarial methods would have incorrectly determined that doing so would have a positive financial impact on the prescription drug plan.

Another exemplary use case relates to channel optimization. Plan members can obtain prescription drugs from various channels including retail pharmacies, specialty pharmacies, and home delivery. The net financial impact to a prescription drug plan can change depending on where and when a particular prescription drug is purchased by a plan member. Using current methodologies, the pharmacy benefit manager does not have the ability to track or analyze how each of these factors may impact the financial outcomes of a prescription drug plan. In contrast, applying the system and method of the present disclosure enables the pharmacy benefit manager to forecast future drug utilization by plan member and customizing this forecast based on the specific channel each plan member purchases prescription drugs and the time of year these purchases are made. This enables the pharmacy benefit manager to forecast the future impact each purchasing channel will have on the prescription drug plan. This forecasting also enables the pharmacy benefit manager to generate an optimum model that will calculate the net impact if the pharmacy benefit manager where to direct plan members to purchase their prescription drugs from certain channels. Armed with this data, the pharmacy benefit manager can now use outreach and marketing methods to target a specific population of the prescription drug plan to drive the purchases being made to those optimal channels.

The system and method described herein provide dynamic tools enabling a large amount of claims data to be assessed, filtered, and processed to convert this claims data into a powerful predictive tool that be can be used to evaluate a wide variety of factors and scenarios that could impact the business of a prescription drug plan. The processed claims data is presented in specific data structures, including various sets of probabilities, to enable these visualizations to be generated. When generating these visualizations, or dashboards, the user may select one or more conditions under which the various models will be run. For example, a user may select the population size to include in the run (between one plan member to all plan members), the number of stochastic iterations, and the first and last months of the model.

The system and method of the present disclosure overcome the limitations of the prior art by utilizing a specific data structure, based on claims data obtained at the individual plan member level, and predictive modeling techniques to forecast future outcomes for the prescription drug plan under a variety of different potential scenarios. Claims data may comprise a wide variety of demographic information and prescription drug event data for each plan member or a prospective plan member (individuals for which claims data is assessed which are not already members of a particular prescription drug plan may be referred to herein as a "patient"). Scenarios that may be simulated include changes to a formulary, changes to which prescription or generic drugs are offered, changes to the purchasing channels of certain prescription drugs, and any other conditions that can affect the drug spend of a prescription drug plan. The system and method disclosed also provide a novel mechanism for resolving the large amount of information associated with claims data to thereby enable these forecasting capabilities using synthetic data to the same level of detail as evaluations based on real historical data.

In an embodiment, a method for generating distributions of potential future outcomes for the prescription drug plan may comprise accessing claims data representative of a patient and determining if the patient is a member of a particular prescription drug plan (a "plan member). If the patient is already a plan member, the method may generate a set of probabilities corresponding to the likelihood that the plan member will leave the prescription drug plan ("disenrollment"). If the patient is not a plan member, the method may generate a set of probabilities corresponding to the likelihood that the patient will become a plan member ("enrollment"). The method may also calculate at least one set of drug activity probabilities representative of at least one of: the likelihood that a plan member will start taking a new drug, continue taking a drug, or stop taking a drug. The method may then run one or more iterations of a stochastic model, using the various probabilities generated for disenrollment, enrollment, and the various drug activities. The outcome of each iteration of the stochastic model may be aggregated to generate distributions forecasting potential future outcomes of the prescription drug plan.

In an embodiment, the present disclosure provides for a non-transitory machine readable medium comprising machine executable instructions, wherein when executed by one or more processors causes the processors to perform a set of instructions. These instructions may comprise accessing claims data representative of a patient and determining whether or not the patient is already a plan member. If the patient is a plan member, the instructions may comprise calculating a set of probabilities corresponding to the likelihood that the plan member will leave the prescription drug plan. If the patient is not a member of the prescription drug plan, the instructions may comprise calculating a set of probabilities corresponding to the likelihood that the patient will become a plan member. The instructions may further cause a processor to calculate at least one set of drug activity probabilities representative of at least one of: the likelihood that a plan member will start taking a new drug, continue taking a drug, or stop taking a drug. The instructions may then cause a processor to run one or more iterations of a stochastic model, using the various probabilities generated for dis-enrollment, enrollment, and the various drug activities and generate distributions of potential future outcomes of the prescription drug plan.

In yet another embodiment, the present disclosure provides for system for predicting potential future outcomes of a prescription drug plan. The system may comprise a database subsystem, which is configured to store claims data representative of a patients which may or may not already be plan members. This database subsystem may be operably coupled to one or more processors which are also operably coupled to one or more prediction subsystems. These prediction subsystems may comprise an enrollment prediction subsystem, a dis-enrollment prediction subsystem, a drug activity prediction subsystem, and an accounting prediction subsystem which are configured to generate one or more sets of probabilities representative of a variety of factors that can impact future performance of a prescription drug plan. One or more processors can manipulate these probabilities to generate various potential future outcomes for the prescription drug plan under a variety of different potential scenarios.

The system and method described herein overcome the limitations of the prior art by enabling pharmacy benefit managers to make detailed decisions based on forecasted data generated at the level of the individual plan member. This novel approach enables pharmacy benefit managers to make informed decisions using information that is not available using state of the art aggregative actuarial methods. Having the ability to generate detailed and accurate forecasts of potential future prescription drug plan outcomes enables the pharmacy benefit manager to target specific populations of plan members based on any number of demographic and prescription drug event data factors to increase profitability of the prescription drug plan and avoid costly mistakes with respect to which prescription drugs are added to a formulary or the channels in which certain prescription drugs are purchased. Forecasting at the individual plan member level may also enable the pharmacy benefit manager to submit more accurate bids to CMS, optimize its supply chain, and market specific products to targeted plan members or plan members in specific geographic locations.

Assessing claims data at the individual plan member level is used because each plan member will differ in terms of when they are enrolled in the prescription drug plan, which diseases and conditions they are receiving treatment for, and the correlation between what prescription drugs they are currently taking and what prescription drugs they will likely take in the future. Assessing the specific point in time the plan members will start or stop taking particular drugs is important because each plan member will progress through various phases of the benefit plan at different rates throughout the course of a given year. Depending on which phase of a benefit plan the plan member may be in (standard, deductible, coverage gap, or catastrophic) when the plan member is or is not taking a particular prescription drug will have an impact on the that plan member's drug spend and therefore impact the overall drug spend of the prescription drug plan. Therefore, there exists a need for a system and method that can provide for more accurate and reliable forecasting of future events that adequately take into consideration prescription drug spend on an individual plan member level at various points throughout a given year. The present methods and systems can use this individual member data to predict the spend on a plan basis, predict when plan members will leave and predict when plan members will be added. Each of three predictions can be made using the present systems and methods. This will provide a more accurate view of the drug events, supply chain needs, pharmacy staffing, plan costs, and financials related to the plan.

The foregoing description describes drug events, pharmacy plans. It is within the scope of the present invention to include other medical plans. Other medical services can be processed using the presently described systems and methods, e.g., when members leave a medical plan, addition of predicted virtual members, and temporal medical services can all be used to model the medical plan.

Figure 11:
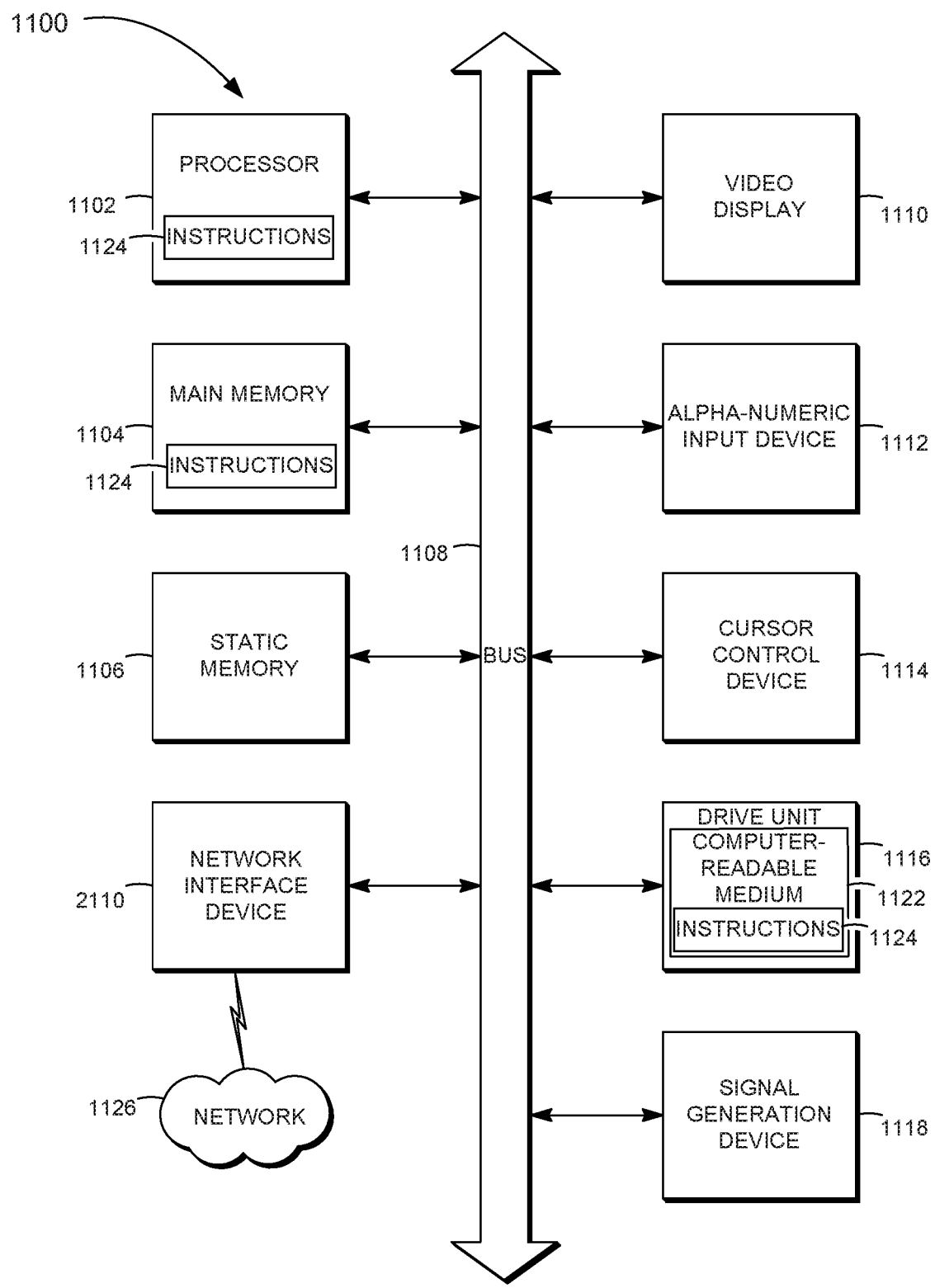
FIG. 11 is a block diagram of a machine in the example form of a computer system within which a set of processor-executable instructions for causing the machine to perform any one or more than one methodologies discussed herein may be executed or stored.

FIG. 11 shows a block diagram of a computer system 1100 within which a set of instructions may be executed causing the machine to perform any one or more than one methods, processes, operations, or methodologies discussed herein. For example, the system 1100 may develop the model and run iterations of the model to determine effects of enrollment, de-enrollment and drug usage probabilities in the drug plan for a time period. These devices and systems are dedicated to performing any one or more than one methods, processes, operations, or methodologies discussed herein.

In an example embodiment, the machine operates as a standalone device or may be connected (e.g., networked, etc.) to other machines. In a networked deployment, the machine may operate in the capacity of a server or a client machine in server-client network environment, or as a peer machine in a peer-to-peer (or distributed) network environment.

The example computer system 1100 includes a processor 1102 (e.g., a central processing unit (CPU), a graphics processing unit (GPU) or both, etc.), a main memory 1104 and a static memory 1106, which communicate with each other via a bus 1108. The computer system 1100 further includes a video display unit 1110 (e.g., a liquid crystal display (LCD) or a cathode ray tube (CRT), etc.). The computer system 1100 also includes an alphanumeric input device 1112 (e.g., a keyboard, etc.), a cursor control device 1114 (e.g., a mouse, etc.), a drive unit 1116, a signal generation device 1118 (e.g., a speaker, etc.) and a network interface device 1120.

The drive unit 1116 includes a computer readable medium 1122 on which is stored one or more than one sets of instructions (e.g., software 1124, etc.) embodying any one or more than one methodologies or functions described herein. The instructions 1124 may also reside, completely or at least partially, within the main memory 1104 and/or within the processor 1102 during execution thereof by the computer system 1100, the main memory 1104 and the processor 1102 also constituting non-transitory computer readable media. When loaded with the instructions 1124, the processor 1102 is a machine dedicated to only the present processes and methodologies.

The instructions 1124 may further be transmitted or received over a network 1126 via the network interface device 1120.

While the computer-readable medium 1122 is shown in an example embodiment to be a single medium, the term "computer-readable medium" should be taken to include a single medium or multiple media (e.g., a centralized or distributed database, and/or associated caches and servers, etc.) that store the one or more than one sets of instructions. The term "computer-readable medium" shall also be taken to include any medium that is capable of storing or encoding a set of instructions for execution by the machine and that cause the machine to perform any one or more than one methodologies of the present invention. The term "Computer-readable medium" shall accordingly be taken to include, but not be limited to, solid-state memories, and optical media, and magnetic media. In some embodiments, the computer-readable medium is a non-transitory computer-readable medium. In other examples, a computer-readable medium is any medium that satisfies statutory requirements and stores instructions for use by a machine.

The present description focuses on prescription drugs and their relationship to a prescription drug plan. It will be recognized that the present systems and methods can be used to evaluate medical plans in addition to prescription drug plans. The prediction device 145 can implement instructions to evaluate data in the data store 105 that relate to medical data and medical plans.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more than one steps within a method may be executed in different order (or concurrently) without altering the principles of the present disclosure. Further, although each of the embodiments is described above as having certain features, any one or more than one of those features described with respect to any embodiment of the disclosure can be implemented in and/or combined with features of any of the other embodiments, even if that combination is not explicitly described. In other words, the described embodiments are not mutually exclusive, and permutations of one or more than one embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more than one intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In this application, including the definitions below, the term 'module' or the term 'controller' or the term 'processor' may be replaced with the term 'circuit.' The term 'module' may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more than one interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuitry that, in combination with additional processor circuits, executes some or all code from one or more than one modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more than one modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a computer to execute one or more than one particular functions embodied in computer programs or computer instructions. The functional blocks and flowchart elements described above serve as software algorithms or specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more than one operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

The methods described herein do not have to be executed in the order described, or in any particular order. Moreover, various activities described with respect to the methods identified herein can be executed in serial or parallel fashion. Although "End" blocks may be shown in the flowcharts, the methods may be performed continuously.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A computer system comprising:
a memory device configured to store a database including, for a plurality of users, user data and historical data; and
at least one processor communicatively coupled to the memory device, the at least one processor configured to:
generate synthetic historical data, in response to receiving a request indicating a group type and a time frame, by:
selecting a set of users from the plurality of users based on the group type;
retrieving, for the plurality of users, the user data and the historical data, to create retrieved user data and retrieved historical data;
identifying a set of new users of the plurality of users during the time frame based on the retrieved user data and the retrieved historical data;
adding the set of new users to the set of users, to generate an updated set of users; and
generating the synthetic historical data for at least one user from the updated set of users;
for the at least one user from the updated set of users, compute a likelihood of a prescription drug event, based on the synthetic historical data corresponding to the prescription drug event;
estimate, for the group type, an aggregated output based on the likelihood of a prescription drug event for the at least one user from the updated set of users;
present the aggregated output via a display device, for the at least one user from the updated set of users;
in response to a correlation between the prescription drug event and a second prescription drug event, compute a second likelihood of the second prescription drug event based on the synthetic historical data corresponding to the second prescription drug event;
estimate, for the group type, the aggregated output based on the likelihood of the second prescription drug event;
present the aggregated output via the display device, for the at least one user from the updated set of users, based on the second likelihood of the second prescription drug event;
compute a third likelihood of discontinuation of one or more drugs based on the synthetic historical data corresponding to the discontinuation, wherein the prescription drug event comprises the discontinuation; and
compute a fourth likelihood of initiation of at least one drug based on the synthetic historical data corresponding to the initiation, wherein the second prescription drug event comprises the initiation.

2. The computer system of claim 1, wherein the prescription drug event comprises the at least one user from the updated set of users being prescribed a first medication; and
wherein the second prescription drug event comprises the at least one user from the updated set of users being prescribed a different, second medication responsive to being prescribed the first medication.

3. The computer system of claim 1, wherein the prescription drug event comprises the at least one user from the updated set of users initiating taking a first prescribed medication; and
wherein the second prescription drug event comprises the at least one user from the updated set of users ceasing to take a second prescribed medication.

4. The computer system of claim 1, wherein the prescription drug event comprises the at least one user from the updated set of users enrolling or dis-enrolling into a pharmacy benefit plan; and
wherein the second prescription drug event comprises the at least one user from the updated set of users enrolling or dis-enrolling into a pharmacy benefit plan.

5. The computer system of claim 1, wherein the database stores baseline data including a third likelihood that a user will enroll or dis-enroll from a corresponding group type; and wherein the at least one processor is further configured to identify the at least one user from the updated set of users based on the baseline data.

6. The computer system of claim 5, wherein the at least one processor is further configured to:
identify a dis-enrolled set of users of the set of users from the group type during the time frame based on the retrieved user data, the retrieved historical data, and the baseline data; and
remove the dis-enrolled set of users from the set of users, wherein the updated set of users 1s generated after removing the dis-enrolled set of users.

7. The computer system of claim 6, wherein identifying the dis-enrolled set of users further comprises:
predicting a third likelihood of dis-enrollment for the users of the set of users corresponding to the group type using a logistic regression function during the time frame based on the user data and the historical data; and
identifying the dis-enrolled set of users based on the third likelihood.

8. The computer system of claim 1, wherein the request identifies the set of users;
wherein the group type corresponds to an enrollment criterion including at least one of: (a) an employer and (b) an age range; and
wherein the set of users includes at least one of: (1) an entire population of users corresponding to the group type, (ii) a targeted population of users corresponding to the group type, and (iii) a random or pseudorandom subset of users corresponding to the group type.

9. A method comprising:
in response to receiving a request indicating a group type and a time frame, by at least one processor communicatively coupled to a memory device,
generating synthetic historical data, by:
selecting a set of users from the plurality of users based on the group type;
retrieving, for the plurality of users, user data and historical data, to create retrieved user data and retrieved historical data;
identifying a set of new users of the plurality of users during the time frame based on the retrieved user data and the retrieved historical data;
adding the set of new users to the set of users, to generate an updated set of users; and
generating the synthetic historical data for at least one user from the updated set of users;
for the at least one user from the updated set of users, computing a likelihood of a prescription drug event, based on the synthetic historical data corresponding to the prescription drug event;
estimating, for the group type, an aggregated output based on the likelihood of a prescription drug event for the at least one user from the updated set of users;
presenting the aggregated output via a display device, for the at least one user from the updated set of users;
in response to a correlation between the prescription drug event and a second prescription drug event, computing a second likelihood of the second prescription drug event based on the synthetic historical data corresponding to the second prescription drug event;
estimating, for the group type, the aggregated output based on the likelihood of the second prescription drug event;
presenting the aggregated output via the display device, for the at least one user from the updated set of users, based on the likelihood of the second prescription drug event;
computing a third likelihood of discontinuation of one or more drugs based on the synthetic historical data corresponding to the discontinuation, wherein the prescription drug event comprises the discontinuation; and
computing a fourth likelihood of initiation of at least one drug based on the synthetic historical data corresponding to the initiation, wherein the second prescription drug event comprises the initiation.

10. The method of claim 9, further comprising:
computing the likelihood of the at least one user from the updated set of users being prescribed a first medication, wherein the prescription drug event comprises the at least one user from the updated set of users being prescribed the first medication; and
computing the second likelihood of the at least one user from the updated set of users being prescribed a different, second medication responsive to being prescribed the first medication, wherein the second prescription drug event comprises the at least one user from the updated set of users being prescribed the different, second medication.

11. The method of claim 9, further comprising:
computing the likelihood of the at least one user from the updated set of users initiating taking a first prescribed medication, wherein the prescription drug event comprises the initiating taking a first prescribed medication; and
computing the second likelihood of the at least one user from the updated set of users ceasing to take a second prescribed medication, wherein the second prescription drug event comprises the ceasing to take a second prescribed medication.

12. The method of claim 9, further comprising:
predicting a third likelihood of new users based on users of the plurality of users matching the group type during the time frame using the retrieved user data and the retrieved historical data; and
identifying the updated set of users during the time frame based on the likelihood of new users.

13. The method of claim 9, further comprising:
determining the correlation between the prescription drug event and a second prescription drug event, by:
identifying, based on the retrieved historical data of the plurality of users, a first set of users of the plurality of users prescribed at least one drug, wherein the prescription drug event comprises being prescribed the at least one drug; determining a grouping of the at least one user from the updated set of users and the first set of users based on user data; and
in response to the at least one user from the updated set of users and a first user of the first set of users being in a matching grouping, determining the at least one drug correlates to a second drug for the selected user, wherein the second prescription drug event comprises being prescribed the second prescription drug.

14. A non-transitory, computer-readable medium having instructions thereon, which, when executed by a processor, perform a method comprising:
in response to receiving a request indicating a group type and a time frame, by the processor communicatively coupled to a memory device,
generating synthetic historical data, by:

selecting a set of users from the plurality of users based on the group type;

retrieving, for the plurality of users from the memory device, user data and historical data, to create retrieved user data and retrieved historical data;

identifying a set of new users of the plurality of users during the time frame based on the retrieved user data and the retrieved historical data;

adding the set of new users to the set of users, to generate an updated set of users; and generating the synthetic historical data for at least one user from the updated set of users;

for the at least one user from the updated set of users, computing a likelihood of a prescription drug event, based on the synthetic historical data corresponding to the prescription drug event;

estimating, for the group type, an aggregated output based on the likelihood of a prescription drug event for the at least one user from the updated set of users;

presenting the aggregated output via a display device, for the at least one user from the updated set of users;

in response to a correlation between the prescription drug event and a second prescription drug event, computing a second likelihood of the second prescription drug event based on the synthetic historical data corresponding to the second prescription drug event;

estimating, for the group type, the aggregated output based on the likelihood of the second prescription drug event;

presenting the aggregated output via the display device, for the at least one user from the updated set of users, based on the likelihood of the second prescription drug event;

computing a third likelihood of discontinuation of one or more drugs based on the synthetic historical data corresponding to the discontinuation, wherein the prescription drug event comprises the discontinuation; and computing a fourth likelihood of initiation of at least one drug based on the synthetic historical data corresponding to the initiation, wherein the second prescription drug event comprises the initiation.

15. The non-transitory, computer-readable medium of claim 14, wherein the method further comprises:

computing the likelihood of the at least one user from the updated set of users being prescribed a first medication, by the processor, wherein the prescription drug event comprises the at least one user from the updated set of users being prescribed the first medication; and computing the second likelihood of the at least one user from the updated set of users being prescribed a different, by the processor, second medication responsive to being prescribed the first medication, wherein the second prescription drug event comprises the at least one user from the updated set of users being prescribed the different, second medication.

16. The non-transitory, computer-readable medium of claim 14, wherein the method further comprises:

computing the likelihood of the at least one user from the updated set of users initiating taking a first prescribed medication, by the processor, wherein the prescription drug event comprises the initiating taking a first prescribed medication; and computing the second likelihood of the at least one user from the updated set of users ceasing to take a second prescribed medication, by the processor, wherein the second prescription drug event comprises the ceasing to take a second prescribed medication.

17. The non-transitory, computer-readable medium of claim 14, wherein the method further comprises:

predicting, by the processor, a third likelihood of new users based on users of the plurality of users matching the group type during the time frame using the retrieved user data and the retrieved historical data; and identifying, by the processor, the updated set of users during the time frame based on the likelihood of new users.

18. The non-transitory, computer-readable medium of claim 14, wherein the method further comprises:

determining the correlation between the prescription drug event and a second prescription drug event, by: identifying, based on the retrieved historical data of the plurality of users, a first set of users of the plurality of users prescribed at least one drug, wherein the prescription drug event comprises being prescribed the at least one drug;

determining a grouping of the at least one user from the updated set of users and the first set of users based on user data; and in response to the at least one user from the updated set of users and a first user of the first set of users being in a matching grouping, determining the at least one drug correlates to a second drug for the selected user, wherein the second prescription drug event comprises being prescribed the second prescription drug.

* * * * *